(12) United States Patent
Johannes et al.

(10) Patent No.: US 7,718,601 B2
(45) Date of Patent: May 18, 2010

(54) SHIGA TOXIN B-SUBUNIT AS A VECTOR FOR TUMOR DIAGNOSIS AND DRUG DELIVERY TO $GB_3$ EXPRESSING TUMORS

(75) Inventors: Ludger Johannes, Courbevoie (FR); David Grierson, Versaillies (FR); Sylvie Robine, Vanves (FR); Jean-Claude Florent, Gif-sur-Yvette (FR); Philipe Maillard, Saint-Cyr-L'Ecole (FR); Jacky Roger, Villecresnes (FR)

(73) Assignees: Institut Curie, Cedex (FR); Centre National de la Recherche Scientifique, Cedex (FR); Institut National de la Sante et de la Recherche Medicale, Cedex (FR)

( * ) Notice: Subject to any disclaimer, the term of this patent is extended or adjusted under 35 U.S.C. 154(b) by 960 days.

(21) Appl. No.: 11/046,786

(22) Filed: Feb. 1, 2005

(65) Prior Publication Data

US 2006/0008475 A1 Jan. 12, 2006

Related U.S. Application Data

(63) Continuation of application No. PCT/EP03/09308, filed on Jul. 31, 2003.

(30) Foreign Application Priority Data

Aug. 2, 2002 (EP) .................................. 02291962

(51) Int. Cl.
*C07K 14/00* (2006.01)
*A61K 38/00* (2006.01)
(52) U.S. Cl. .......................................... 514/2; 530/350
(58) Field of Classification Search .................. None
See application file for complete search history.

(56) References Cited

U.S. PATENT DOCUMENTS

| | | | | |
|---|---|---|---|---|
| 4,782,113 A | * | 11/1988 | Maeda et al. | 424/78.21 |
| 4,827,945 A | * | 5/1989 | Groman et al. | 424/9.32 |
| 5,053,423 A | * | 10/1991 | Liu | 514/410 |
| 5,250,565 A | * | 10/1993 | Brooks et al. | 514/443 |
| 5,753,627 A | * | 5/1998 | Albert et al. | 514/16 |
| 5,807,879 A | | 9/1998 | Rosebrough | |
| 5,840,485 A | * | 11/1998 | Lebl et al. | 435/6 |
| 5,994,311 A | * | 11/1999 | Eichner et al. | 514/18 |
| 6,348,446 B1 | | 2/2002 | Gariépy | |
| 6,368,598 B1 | * | 4/2002 | D'Amico et al. | 424/181.1 |
| 7,112,317 B2 | * | 9/2006 | Thorpe et al. | 424/1.49 |
| 2004/0110935 A1 | * | 6/2004 | Johannes et al. | 530/395 |

FOREIGN PATENT DOCUMENTS

| | | | |
|---|---|---|---|
| EP | 1229045 A1 | * | 8/2002 |
| WO | WO97/25067 | * | 7/1977 |
| WO | WO95/11998 | * | 5/1995 |
| WO | WO-00/61183 A | | 10/2000 |
| WO | WO-02/02147 A | | 1/2002 |
| WO | WO-02/060937 A | | 8/2002 |

OTHER PUBLICATIONS

Johannes L et al., The Journal of Biological Chemistry. United States, Aug. 1, 1997, vol. 272, No. 31, pp. 19554-19561.
Schelte P et al., Bioconjugate Chemistry, American Chemical Society, Washington, US, vol. 11, No. 1, Jan. 2000, pp. 118-123.
Haicheur et al., J. of Immunology, vol. 165, No. 6 (2000) pp. 3301-3308 (XP002187748).
Sandvig et al., The EMBO Journal, vol. 19, No. 22 (2000) pp. 5943-5950 (XP002228667).
Haicheur et al., J. of Immunology, vol. 165 (2000) pp. 3301-3308 (XP002228666).

* cited by examiner

*Primary Examiner*—Anand U Desai
(74) *Attorney, Agent, or Firm*—Birch, Stewart, Kolasch & Birch, LLP.

(57) ABSTRACT

The invention relates to new compounds for cancer therapy or diagnosis and to the use of a non-toxic B subunit of Shiga toxin mutant as a vector for diagnostic products or drugs in over-expressing Gb3 receptor cells, such compounds having the following formula: STxB-Z(n)-Cys-Y(m)-T wherein-STxB is the Shiga Toxin B subunit or a functional equivalent thereof, -Z(n) wherein n is 0 or 1, Z is an amino-acid residue devoid of sulfydryl groups, or is a polypeptide, -T is a molecule linked by a covalent bound to the S part of Cys, selected from: agents for in vivo diagnosis, cytotoxic agents, prodrugs, or enzymes for the conversion of a prodrug to a drug, - Y(m) wherein m is 0 or 1, Y is a linker between T and Cys, which is either cleavable or not cleavable for the release of T after the internalization of the hybrid compound into cells.

23 Claims, 16 Drawing Sheets

Figure 1:
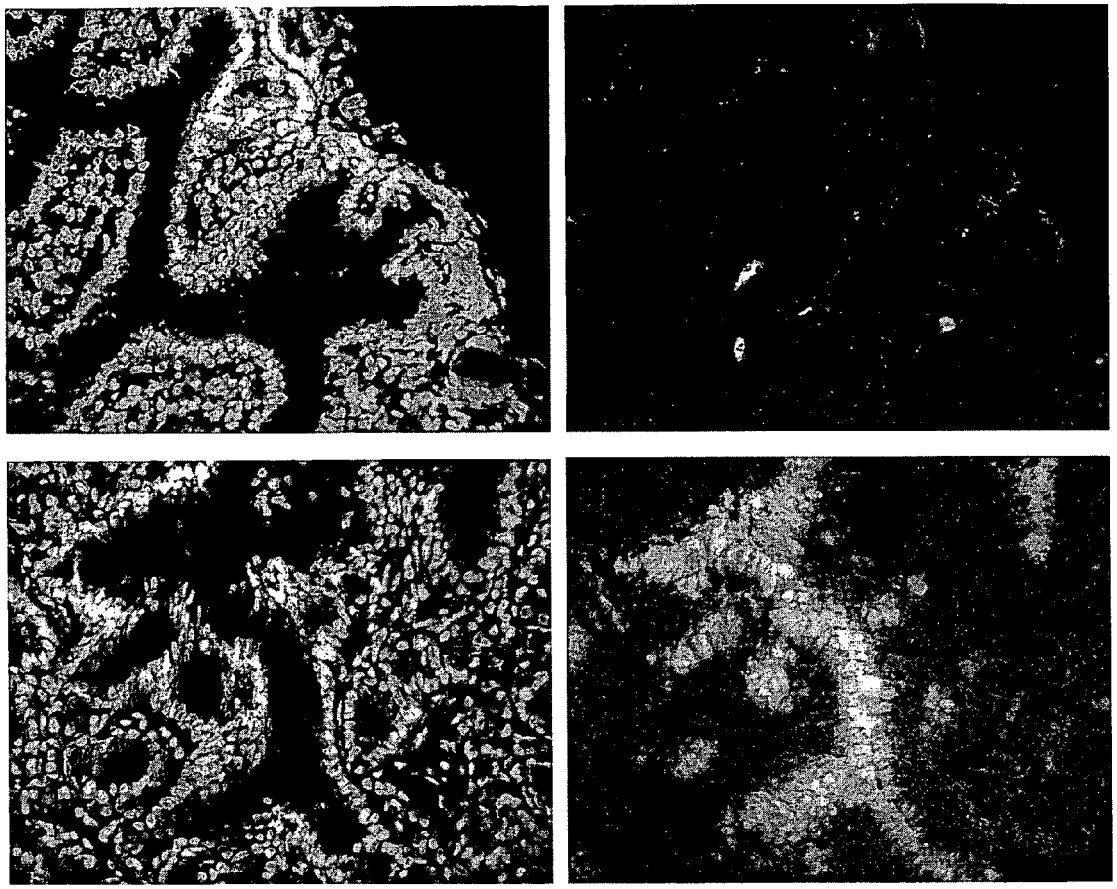

| Category | Surviving Fraction |
|---|---|
| Holo-NCS/Shiga Toxin Conj. in ice + PPMP | ~0.78 |
| Holo-NCS/Shiga Toxin Conj. in ice | ~0.28 |
| Holo-NCS in ice + PPMP | ~0.88 |
| Holo-NCS in ice | ~0.95 |
| Blank + PPMP | ~1.05 |
| Blank | ~0.97 |

Figure 8:

NHS-Ester Reaction Scheme

Maleimide Reaction Scheme

MBS
m-Maleimidobenzoyl-N-hydroxysuccinimide ester

Figure 12

[Graph: Surviving fraction (% of control) vs STxB-Porphyrin (mg/ml). Two curves: −Gb3 (dashed, squares) staying near 90-100%, and +Gb3 (solid, circles) dropping to ~40% at 0.15 mg/ml and decreasing to ~35% at 0.6 mg/ml.]

Figure 15:

SHIGA TOXIN B-SUBUNIT AS A VECTOR FOR TUMOR DIAGNOSIS AND DRUG DELIVERY TO GB₃ EXPRESSING TUMORS

CROSS-REFERENCE TO RELATED APPLICATION

This Nonprovisional application is a continuation of PCT/EP2003/009308 filed on Jul. 31, 2003, which claims priority under 35 U.S.C. §119(a) on Patent Application No. 02291962.5 filed in Europe on Aug. 2, 2002, the entire contents of which are hereby incorporated by reference.

The invention relates to new compounds for cancer therapy or diagnosis and more specifically to the use of a non-toxic Shiga toxin B subunit mutant as a vector for diagnostic products or drugs in $Gb_3$ over-expressing receptor cells.

Despite decades of fundamental and clinical research in the field of oncology, the long-term prospect of patients with aggressive disease remains daunting. One of the principle limitations of current treatments of cancers, chemotherapy and radiotherapy, is the lack of targeting to cancer cells. The most rational and successful approach to targeting involves conjugating specific cancer cell surface ligands (e.g. monoclonal antibodies, peptide hormones, . . . ) with cancer chemotherapeutics, radioactive isotopes, or biological toxins in the hope of promoting their localization in tumor cells.

Cell transformation and oncogenic development are accompanied by changes in the expression and the structure of glycosphingolipids. It is generally believed that these changes are related to the proposed functions of glycosphingolipids in cell adhesion and cellular signaling. Indeed, together with cholesterol, the glycosphingolipids are major components of membrane microdomains (rafts) that play a central role in receptor aggregation and receptor interaction with signaling molecules, such as kinases of the Src family. In addition, a role for glycosphingolipids and membrane microdomains in intracellular sorting is currently evaluated. According to the so-called "raft hypothesis" proposed by Simons and coworkers, asymmetry in the lipid and protein distribution in the lateral plane of membranes contributes to membrane sorting to distinct intracellular destinations.

The GSL globotriaosyl ceramide ($Gb_3$ or CD77) is expressed on a narrow range of committed B cells and associated B cell lymphomas (Gordon et al., 1983; Kalisiak et al., 1991; Mangeney et al., 1991; Murray et al., 1985; Oosterwijk et al., 1991). Indeed, it was recently reported that binding sites for $Gb_3$-specific ligands could be detected on all grades of follicle center cell lymphomas, with more than 70% of patient tumor samples being positive (LaCasse et al., 1999). 30-40% of samples from patients with small lymphocytic lymphomas, large B cell lymphomas, or multiple myeloma were also found to be positive. Ovarian hyperplasias (Arab et al., 1997) and cell suspensions obtained from human breast tumors (LaCasse et al., 1999) were tested positive for $Gb_3$. Finally, $Gb_3$ was also markedly increased in a number of cell lines derived from human astrocytomas (Arab et al., 1999).

In the light of the described $Gb_3$ expression on human cancer cells it is tempting to propose the use of the lipid for vectorization purposes. Natural ligands of $Gb_3$ have been described, encompassing the bacterial protein toxins Shiga toxin from *Shigella dysenteriae* and the verotoxins from *Escherichia coli* (Lingwood, 1996; Sandvig and van Deurs, 1996). These toxins are composed of two subunits. The enzymatic A-subunit modifies ribosomal RNA thus leading to an inhibition of protein biosynthesis. For cellular binding and intracellular transport, the A-subunit has to interact with the non-toxic B-subunit, a homopentamer of 5 B-fragments. The B-subunit binds, under certain conditions in a cooperative manner, to 10-15 $Gb_3$ molecules. This clustering leads to the association of the toxin with membrane microdomains, an important event for the intracellular trafficking of the toxin (Falguières et al., 2001). In toxin sensitive cells, Shiga toxin and its non-toxic B-subunit are targeted by retrograde transport from the plasma membrane to the endoplasmic reticulum, via the early endosome and the Golgi apparatus (for a review, see (Johannes, 2002)). At the level of the endoplasmic reticulum, the A-subunit then passes via retrotranslocation across the membrane into the cytosol. It is important to note that some cell types are resistant to the action of the toxin, despite the expression of $Gb_3$ (Falguières et al., 2001). This is likely related to an altered intracellular transport pattern in these cells (Falguières et al., 2001).

Shiga Holotoxin has been described as an anti-tumor agent in xenograft transplants in mice (Arab et al., 1999). Furthermore, it eliminates clonogenic tumor cells in purging applications (LaCasse et al., 1996). However, the use of the holotoxin as a therapeutic agent has important limitations. First, the action of the A-subunit of the toxin is not tumor cell specific. Second, the holotoxin is a large protein whose capacity to infiltrate solid tumors is limited. Third, a large bacterial protein as the holotoxin leads to an efficient immune response. Forth, the necessity to maintain simultaneous $Gb_3$ and A-subunit binding limits the possibility to introduce mutations that favor immune evasion or intracellular targeting.

In this invention, we have therefore used the B-subunit of Shiga toxin as a cancer cell vectorization means, in the absence of the A-subunit. A previously constructed B-subunit mutant was used that allows site directed chemical coupling to the B-subunit, preserving its interaction with $Gb_3$.

More particularly, the B-subunit mutant, or derivative named STxB-Z(n)-Cys, wherein n is 0 or 1, has been designed. In this protein, a Cysteine is added at the C-terminus of mature STxB. The protein, when purified from bacteria, carries the internal disulfide bond, as wild type STxB, while the sulfhydryl group at the C-terminal Cys is free. Due to their nucleophilicity, free sulfhydryl groups are excellent acceptors for directed coupling approaches (Philippe Scheltè et al., 1999).

These mutants can be used as universal carriers for targeting molecules to $Gb_3$ receptor expressing cells.

Thus, the present invention relates to an hybrid compound for the diagnosis or therapy of cells over-expressing the receptor $Gb_3$, having the following formula: STxB-Z(n)-Cys-Y(m)-T, wherein:
- STxB is the Shiga Toxin B subunit or a functional equivalent thereof,
- Z(n) werein n is 0 or 1 and when n is 1, Z is an amino-acid residue devoid of sulfydryl group or is a polypeptide,
- Cys is the amino-acid residue for Cysteine,
- T is a molecule linked by a covalent bound to the S part of Cys, selected in a group comprising:
  - agents for in vivo diagnosis,
  - cytotoxic agents,
  - prodrugs, or
  - enzymes for the conversion of a prodrug to a drug,
- Y(m) wherein m is 0 or 1 and when m is 1, Y is a linker between T and Cys, said linker being either cleavable or not cleavable for the release of T after the internalization of the hybrid compound into said cells.

In the invention, T is thus operably linked to Cys either directly through covalent binding or indirectly through a linker, Y, allowing or not said release of T moiety.

In a preferred embodiment, Z(n) is such that n=0, and the STxB-Z(n)-Cys moiety of the hybrid compound has the following sequence (SEQ ID No 1):
COOHMKKTLLIAASLSFFSASALATPDCVTGKVE YTKYNDDDTFTVKVG

DKELF TNRWNLQSLLLSAQITGMTVTIKTNACHNGGGFSEVIFRC-NH2

When Z(n) is such that n=0, the above moiety is also expressed as STxB/Cys.

As a matter of fact, if the Z moiety is too long, i.e., when n is equal or greater than 2, some internal disulfide bridges might occur, and prevent the binding of STxB to the Gb3 receptor and especially prevent the binding to the molecule of interest.

The invention results from the observation that cancer cells, and more particularly tumors, and more particularly intestinal and colorectal tumors, over-express $Gb_3$ receptor, as can be seen in, FIG. 1, FIG. 2 and FIG. 10 hereinafter. $Gb_3$ is not present in normal intestinal epithelia in humans (Jones et al., 2000). Accordingly, it has been shown that $Gb_3$ is present in low to undetectable levels in mouse. On the contrary, $Gb_3$ is over-expressed in the human colon cancer cell line CaCO2 (Jones et al., 2000). Thus, it constitutes an excellent marker to distinguish between tumor cells and normal intestinal cells both in humans as well as in murine models. This differential pattern of $Gb_3$ expression provides the basis for the new therapeutic and diagnostic developments of the present invention in colorectal cancer, and more generally in any $Gb_3$ over-expressing tumor or cancer cell. Over expression of Gb3 receptor on cells can be assessed by carrying out a method such as that disclosed in Example 1 when assessing the mouse model, especially starting from biopsy material. Another method encompasses performing an MRI for determination of Gb3 distribution. In some situations however, confirmation that the tumor to be treated is a Gb3 over-expressing tumor is not specifically sought prior to initiating the treatment.

According to the invention, the expression "therapeutic treatment" encompasses the action of the hybrid compound of the invention which results in a beneficial effect for the patient undergoing the treatment, said effect being either obtained at a cellular level or at a clinical level, including encompassing as a result an improvement of the condition of the patient or a remission state or a recovery of a health state. In the present invention, said therapeutic treatment is provided to a patient having a tumor and especially suffering from a cancer.

According to the invention, the expression "diagnosis" encompasses the detection of a pathological state or the detection of one or several parameters which may be correlated either directly or indirectly, possibly in combination with other parameters, to a pathological state and which may provide information useful in a diagnostic protocol. The expression also encompasses the possible quantitative detection of parameters related to such a pathological state.

In one embodiment, the hybrid compounds of the invention can bear a T moiety which is a contrast agent for the detection of $Gb_3$ —expressing cancer cells by life-imaging techniques such as Magnetic Resonance Imaging (MRI). Other non-invasive life imaging techniques include two-photon microscopy, contrast enhanced ultrasound, contrast enhanced X-ray, computed tomography, isotope scanning, contrast enhanced thermography.

More particularly, said contrast agents can be selected in a group comprising paramagnetic compounds, such as porphyrin-gadolinium, porphyrin-manganese, synthetic polymer-gadolinium, gadolinium-ethoxybenzyl-diethylenetriamine-pentaacetic acid, DOPTA-gadolinium, ferrofluide and nanoparticules, which are then administrated to humans or animals.

The present invention also pertains to the use of such compounds for in vivo diagnosis of tumors, more specifically for MRI diagnosis. The use is advantageous for intestinal and colorectal cancers as far as it has been shown that $Gb_3$ receptors are expressed specifically in cancer cells but not in normal cells.

In another embodiment, the hybrid compounds of the invention can bear as a T moiety a tumor specific drug or pro-drug which is vectorized to tumor-specific transport pathways in $Gb_3$-positive cancer cells allowing the increase of the efficiency and/or specificity of these treatments. T moiety might also be a pro-drug activator while the pro-drug alone is administered directly by any known drug delivery system, i.e. by systemic, transdermic, oral, rectal administration.

Overall, the use of the B-subunit as a cancer targeting means has the following advantages. First, due to its small size, tissue penetration with the B-subunit is efficient. Second, the antibody response to the B-subunit is inefficient. Third, tumor-selective compounds can be coupled to the B-subunit. Forth, tumor-specific transport pathways can be exploited to increase the efficiency of the treatment. Fifth, when modifications of the B-subunit are done, only $Gb_3$ binding ability needs to be preserved.

In one aspect of invention, the drug is a photosensitizing drug suitable for Dynamic Phototherapy (DPT). DPT is a recently developed technique for the treatment of solid human tumors. It is based on the targeting to and photoactivation of dyes such as porphyrins or related system within tumor tissue. The molecular events are beginning to be understood, such as cellular death through apoptbsis and other mechanisms, implicating mitochondria, nuclei, . . . Some photosensitizing drugs are already used in the clinics (Photofrin®, Foscan®, . . . ). However, these substances have a number of drawbacks, most notably the absence of tumor-specific targeting. Several strategies have been proposed to improve the tumor selectivity of photosensitizers. They include the use of adapted delivery systems such as liposomes, lipoproteins, monoclonal antibodies, nanoparticules to modify biodistribution of dyes. Another approach developed at the Institute Curie is to modulate the amphiphilicity of the macrocycle. Structural modifications induced by glyco-conjugation of the tetrapyrrolic system is an effective means to create a balance between hydrophilicity and hydrophobicity. Following this approach, neutral tri- and tetra-glycoconjugated tetrapyrrolic macrocycles were prepared and evaluated in vitro for their photocytotoxicity (Momenteau et al., 1999).

Therefore, a glycoconjugated, relatively hydrophilic tetrapyrrolic macrocycle (porphyrin) has been synthesized, which carries a bromo-benzyl group that allows coupling to STxB/Cys. Synthesis, coupling to STxB/Cys, and purification of the resulting compound are described hereunder. When achieving contact with tumor cells, the therapeutic compound composed of STxB/Cys and the glycoconjugated porphyrin accumulates stably in the endoplasmic reticulum and the Golgi apparatus. The phototoxicity of the porphyrin can then be activated locally by irradiation with visible light after the clearance of the cytotoxic compound from cells that need to be preserved, such as dendritic cells in which STxB does not target the retrograde route (Falguières et al., 2001).

In another aspect of the invention, T is a cytotoxic agent. Said cytotoxic agent might be toxic for the cell after internalization either directly, or indirectly through the action of a second component, said second component acting as a mean for transforming a pro-drug into a cytotoxic drug.

One example of cytotoxic agent is Neocarzinostatin (NCS). In this case, m=0 and T is the holo-NCS.

Holo-neocarzinostatin (holo-NCS) is the prototype of the protein antibiotic family. It is a 11.3 kDa complex consisting of a dodecadiyne antibiotic ($NCS_{Chrom}$) which contains the cytotoxic activity, reversibly bound to a carrier protein known as apo-neocarzinostatin (apo-NCS) (for a review, see (Favaudon, 1982)). Holo-NCS is active in the nanomolar range, and $NCS_{Chrom}$ cleaves DNA in the course of a suicide reaction leaving no residual active drug after a few minutes incubation. No resistance to $NCS_{Chrom}$ associated with reduced drug import (MDR) has been reported.

The major DNA lesions induced by $NCS_{Chrom}$ in DNA result from radical attack and consist of a blunt end break bearing a thymidine-5'-aldehyde residue on one strand, with an abasic site at two nucleotide interval on the complementary strand. This abasic site is substrate for endonuclease III in such a way that $NCS_{Chrom}$-induced damage is very rapidly converted into DNA double-strand breaks in living cells. Mutants of E. coli, yeast or mammalian cells defective in any pathway of double-strand break repair, most notably through a defect in DNA-dependent protein kinase, are consistently hypersensitive to induced cell kill by NCS.

The purification of NCS, the method of obtaining the hybrid compound wherein NCS is covalently linked to Cys, and the cytotoxic effect of this hybrid compound are illustrated in example 1 hereinafter.

In another embodiment of the hybrid compounds of the invention, T is a prodrug and m=1. Prodrugs are defined as therapeutics agents which are inactive but are transformed in active metabolites by biotransformation. The pro-drug is then transformed by a second component inside the cell after internalization of the hybrid compound. Said second component might be a cell metabolite such as an enzyme. An exemple of this embodiment is an hybrid compound wherein T is a cytotoxic drug such as anthracyclins (daunomycin, doxorubicin, daunorubicin . . . ), idarubicin, cis-platinium, mitomycin C, desacetylvinblastine, methotrexate, N-acetylmelphan, 5-fluorouracil, nitrogen mustards, calicheamicin, maytansinodids, and Y is a linker sensitive to an endogenous enzyme such as a mannosidase.

Another embodiment includes the approach described by (Saxon and Bertozzi, 2000). A sugar precursor containing an azido group is targeted to cancer cells via STxB/Cys. After liberation of the azido-carrying sugar in the Golgi apparatus, the later is integrated into carbohydrate chains of the cancer cell. In interaction with a phosphin-carrying prodrug, a therapeutic compound is released that specifically acts in the tumor environment Another embodiment includes the use of amidoximes (N-Hydroxyamidines) as pro-drugs, cleavable by endogeneous reductases.

Several reductases are responsible for the reduction of amidoximes to amidines. A microsomal enzyme system has been purified from pig and human liver consisting of cytochrome b5, its reductase and a P450 isoenzyme (Clement B et al., 1997). A similar enzyme system is present in mitochondria. Reductive activities are located in several organs such as liver, kidney, lung and even brain.

In another formulation, prodrugs are made incorporating linkages that are sensitive to mannosidase. The prodrugs are coupled to STxB/Cys and targeted to $Gb_3$ expressing cancer cells. In this case, the activation of the prodrug occurs in the Golgi apparatus of the cancer cell using endogenous mannosidase without prior vectorization of the enzyme.

In another embodiment, the said second component in an hybrid compound according to the invention wherein T is an enzyme for the transformation of the pro-drug into drug, when said enzyme is not present endogeneouly or is not present in the targeted compartment of the cell, i.e. the golgi apparatus.

One example is the use of prodrugs that contain glucoronic acid conjugated through a linker moiety to the aminoglycoside of doxorubicin. Such prodrugs are synthesized as described in (Bakina and Farquhar, 1999). The anthracycline prodrug can be converted to doxorubicin by β-glucuronidase. In this case, the T moiety of the second coumpound is the β-glucuronidase. In a first step, β-glucuronidase is coupled to STxB/Cys as described hereunder for BSA and NCS. The coupling product is targeted to the Golgi apparatus (FIG. 13) and the endoplasmic reticulum of $Gb_3$ expressing tumors cells and retained in this compartment. In other cells, such as dendritic cells, the coupling product is rapidly degraded (Falguières et al., 2001). In a second step, -the prodrug is coupled to STxB/Cys. The product can be activated in cells that have retained the STxB/Cys-β-glucuronidase coupling product (cancer cells), but not in cells that have lost this product (dendritic cells).

In another embodiment, the prodrug is a nucleotide analog which, after enzymatic transformation, can be incorporated into the replicating DNA and stop said replication. Such prodrugs for gene suicide cancer therapy are reviewed in Singhal S. et al. (1999). One example is an hybrid compound wherein T is Ganciclovir (GCV) or acyclovir (ACV), and Y is a linker cleavable by an endogeneous enzyme such as mannonidase. The second component is a second hybrid compound wherein T is the Thymidine kinase of Herpes Simplex Virus ($HSV_1$-TK). This enzyme can convert GCV or ACV to GCV monophosphate or ACV-monophosphate. These monophosphate nucleosides are then phosphyrylated to diphosphate and to tri-phosphate nucleotide analogs by endogeneous kinases. GCV-triphosphate lacks the 3'OH on the deoxyribose as well as the bond between the 2'and 3'carbons which are necessary for DNA chain elongation. A a result, GCV-triphosphate integration causes premature DNA chain termination and leads to apoptosis.

Thus, the present invention encompasses also:

hybrid compounds wherein Y is an enzyme cleavable linker selected in a group comprising reduced and non-reduced folates cleavable by carboxypeptidase G, phosphate groups from phosphorylated prodrugs cleavable by alkaline phosphatase, hydrolytic cleavable compounds by carboxypeptidase A, nitroreductase for prodrug activation, hydrolysis of lactam ring cleavable by beta-lactamase, amide cleavable by penicillin amidase, cytosine deamidase for prodrug activation, glucoronic acid cleavable by beta-glucoronidase, galactose cleavable by galactosidase, mannose cleavable by mannosidase.

hybrid compounds wherein Y is selected in a group comprising non-selective linkers such as glutaric acid, dianhydride of diethylenetriaminepentaacetic acid, carbodiimide . . . , acid cleavable linker such as cis-aconitic anhydride, acyl hydrazones, Schiff bases, trityl linkers, lysosomally degradable, disulfide, linkers such as SPDP.

The skilled person can easily adapt this strategy of prodrug conversion using the Hybrid compounds according to the invention to any known pro-drug principle, and more particularly to the multiple and complementary suicide therapies. The synergistic effect of the multiple suicide strategy enables lower doses or individual drugs for maximum sensitivity and reduces cytotoxicity in nontransduced cells. Furthermore, development of resistance to the suicide strategy is greatly reduced when two (or more) separate pathways are targeted.

The present invention pertains to the use of an hybrid compounds of the formula STxB-Z(n)-Cys-Y(m)-T for the therapies of $Gb_3$ expressing cells. One example of these cells are intestinal, and particularly colorectal cells which express $Gb_3$ receptor only when they are tumor cells.

Accordingly, STxB-Z(n)Cys-Y(m)-T as defined in the present invention provides means for therapy of pathogenic states including tumors or cancer associated with over-expression of Gb3 receptor on tumor cells.

The present invention also pertains to pharmaceutical compositions containing at least one hybrid compound of the formula STxB-Z(n)-Cys-Y(m)-T for the diagnosis or therapy of cancers having over expressing $Gb_3$ receptor cells, in combination with acceptable pharmaceutical carriers.

It should be understood herein that pharmaceutical compositions apply either for in vivo diagnosis or for therapy of cancers cells or tumors and might contain any of the hybrid compounds described herein.

A pharmaceutical composition according to the invention advantageously comprises one or more components to be administered in one step or sequentially in time. For example, a first component of the pharmaceutical composition contains as an active component an hybrid compound wherein T is an enzyme, and for example β-glucoronidase which is first administered to a patient bearing a tumor having over-expressing $Gb_3$ receptor cells; this first component is administered once to such patients; the second component of the pharmaceutical composition contains an hybrid compound according to the invention wherein T is a prodrug and Y is glucuronic acid; this second component of the pharmaceutical composition might be administered to the patient sequentially in the time with repetited administrations to obtain a long term effect of the therapy.

A pharmaceutical composition according to the invention is particularly interesting for the treatment of intestinal tumors and more particularly for colorectal tumors as far as, it has been demonstrated herein, first that these tumors express specifically $Gb_3$ receptor and second that the pharmaceutical compositions bearing pharmaceutical carriers for oral or rectal administration are effective after an oral or rectal administration of the pharmaceutical composition.

The present invention also pertains to a method for inducing the death of cancer cells bearing over expressing $Gb_3$ receptors, the method comprising administering an effective amount of at least one hybrid compound described herein above, such that cancer cells death occurs.

Accordingly, the invention relates in particular to means suitable for in vivo diagnosis of tumor or in vivo diagnosis of cancer.

The invention also pertains to a method for in vivo diagnosis of cancer or tumor cells over-expressing $Gb_3$ receptor, this method comprising administering an effective amount of an hybrid compound having a T moiety which is a contrast agent.

The method for the manufacturing an hybrid compound of the invention is described in PCT/EP 02/01627. Briefly:

The universal part of the hybrid compound, i.e, STxB-Z(n)-Cys might be manufactured by a recombinant cell line obtained by transformation with a recombinant vector or plasmid comprising a polynucleotide sequence encoding the STxB-Z(n)-Cys part of the hybrid compound. More particularly, the sequence including such molecule is an isolated polynucleotide selected from the group of:

(a) a polynucleotide comprising the nucleotide sequence STxB encoding the Shiga Toxin B subunit or a functional equivalent thereof bearing at its 3'end the codon TGT, or the codon TGC encoding Cysteine;

b) a polynucleotide comprising a nucleotide sequence having at least 80% sequence identity to a nucleotide sequence encoding the Shiga toxin B-subunit or a functional equivalent thereof bearing at its 3'end the codon TGT or TGC; and c) a nucleotide sequence complementary to the sequence in a) or b).

The coupling approaches for covalent binding of —Y(m)-T moiety to STxB-Z(n)-Cys, m being 0 or 1, can be any method or processes described or carried out by a skilled person.

A first method that can be embodied is the use of SPDP hetero-bi-functional cross-linker described par Carlsson et al. However, SPDP is capable of being cleavable by serum thiolases that is a cause of decreasing the yield of the reaction.

A second method for covalent coupling of STxB -Z(n)-Cys peptides with another peptide of interest is to produce bromoacetyl or maleimide functions on the latter as described by P. Schelte et al. Briefly, the peptide of interest is chemically activated with bromoacetate anhydride or by a maleimide group respectively. In appropriate reaction conditions (pH, temperature, incubation times), these groups are eliminated by cis-elimination, yielding respectively to —S—S—, —S—CH$_2$—, to —S—CO— or to —S—NH— covalents linkages.

As an example, the polypeptide or the peptide to be coupled to the —SH moiety the C-terminal Cysteine of the universal carrier, has its N-terminus activated with bromoacetic anhydride following the reaction scheme:

$$B_R-CH_2-CO-O-CO-CH_2-B_R+$$
$$NH_2-_{PEPTIDE} \Rightarrow B_R-CH_2-CO-NH-_{PEPTIDE}+$$
$$B_R-CH_2-COOH$$

The Bromoacetyl function has high chemoselectivity for peptide thiol groups and the activated peptide can be reacted with STxB-Cys as follows:

$$STxB-Cys-SH+Br-CH_2-CO-$$
$$NH\text{-peptide} \Rightarrow STxB-Cys-S-CH_2-CO-NH\text{-peptide}+HBr$$

The resulting thioether-linkage is stable to hydrolysis.

Figure 9:
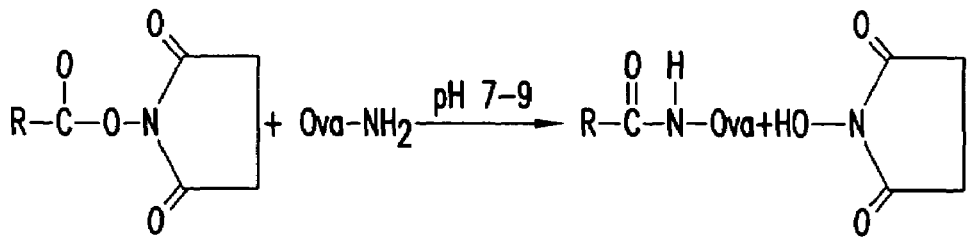
Figure 9:
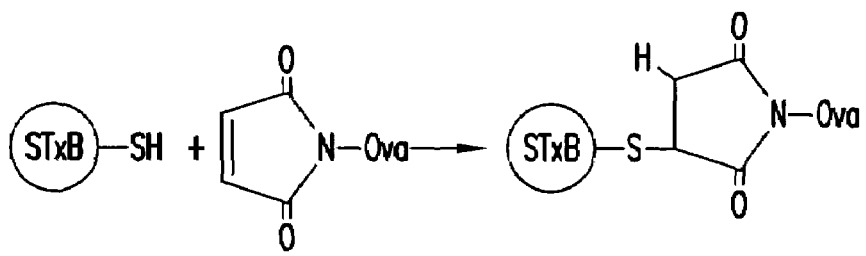
Figure 9:
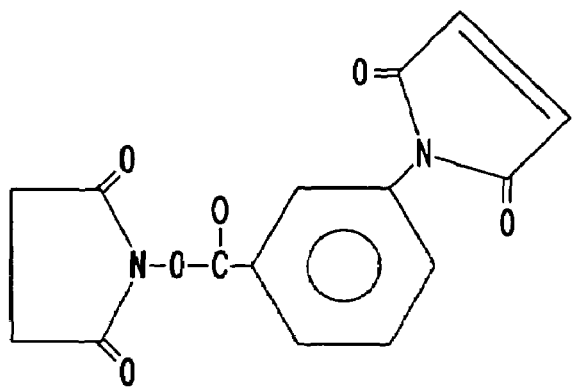

Another method for coupling a molecule to the universal carrier of the invention is to use MBS (m-Maleimidobenzoyl-N-hydroxysuccinimide ester) as shown in FIG. 9. This coupling allows the transport and processing of large molecules such as enzymes.

Another example for the coupling of complex molecules such as metalloporphyrines is shown in example 2 herein after.

Without limiting the scope of the hybrid compounds of the invention, their use and the pharmaceutical compositions, the hereinafter examples and figure illustrate the advantages of the present invention.

LEGENDS OF THE FIGURES

FIG. 1: Uptake of STxB by intestinal tumors after 2.5 h, comparison with normal tissue. Upper panels: normal duodenum. lower panels: tumor from the periampullar region. Left panels: nuclei are stained with Hoechst dye. Right panels: anti-STxB staining.

Figure 2:
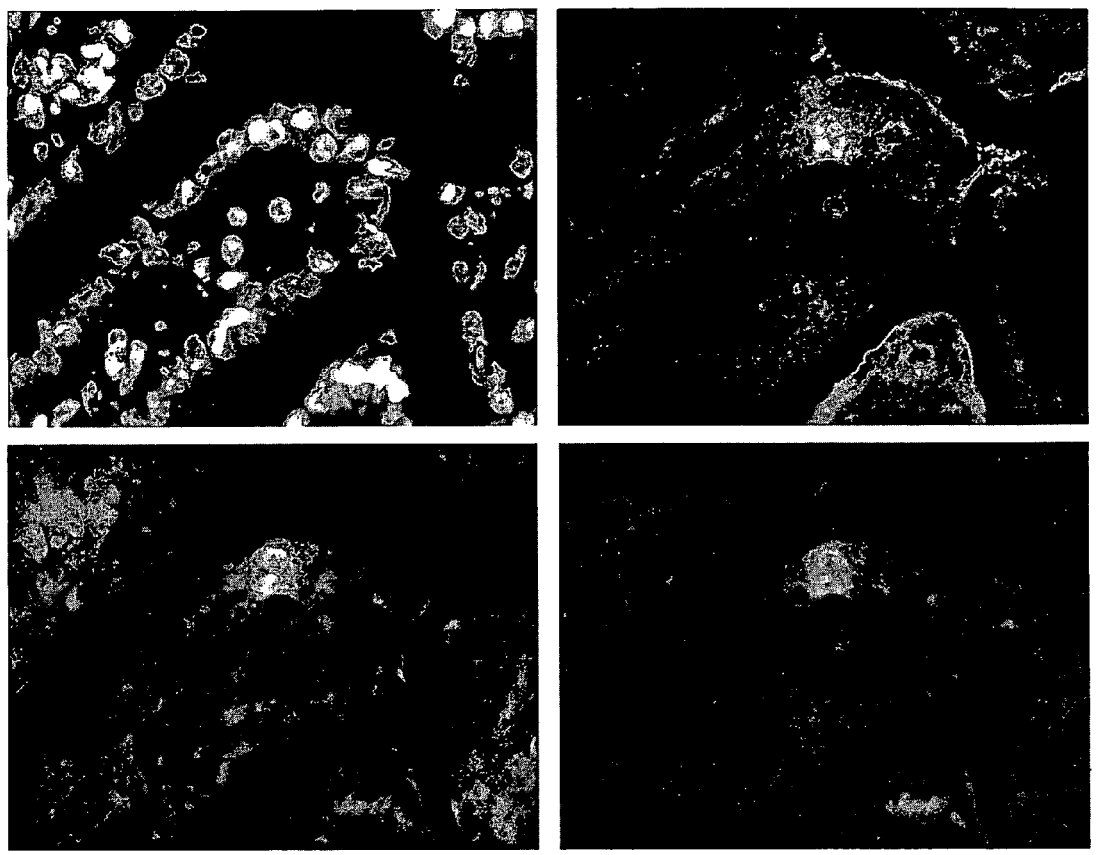

FIG. 2: In normal tissue, enteroendocrine cells take up STxB. A region from normal duodenum is shown. nuclear staining with Hoechst (upper left panel), anti-chromogranin A/B antibody (upper right panel) and anti-STxB antibody (lower left panel). Lower right panel shows a superposition of the three stainings: nuclei (blue), chromogranin A/B (red), STxB (green). Yellow color demonstrates colocalisation of chromogranin and STxB.

Figure 3:
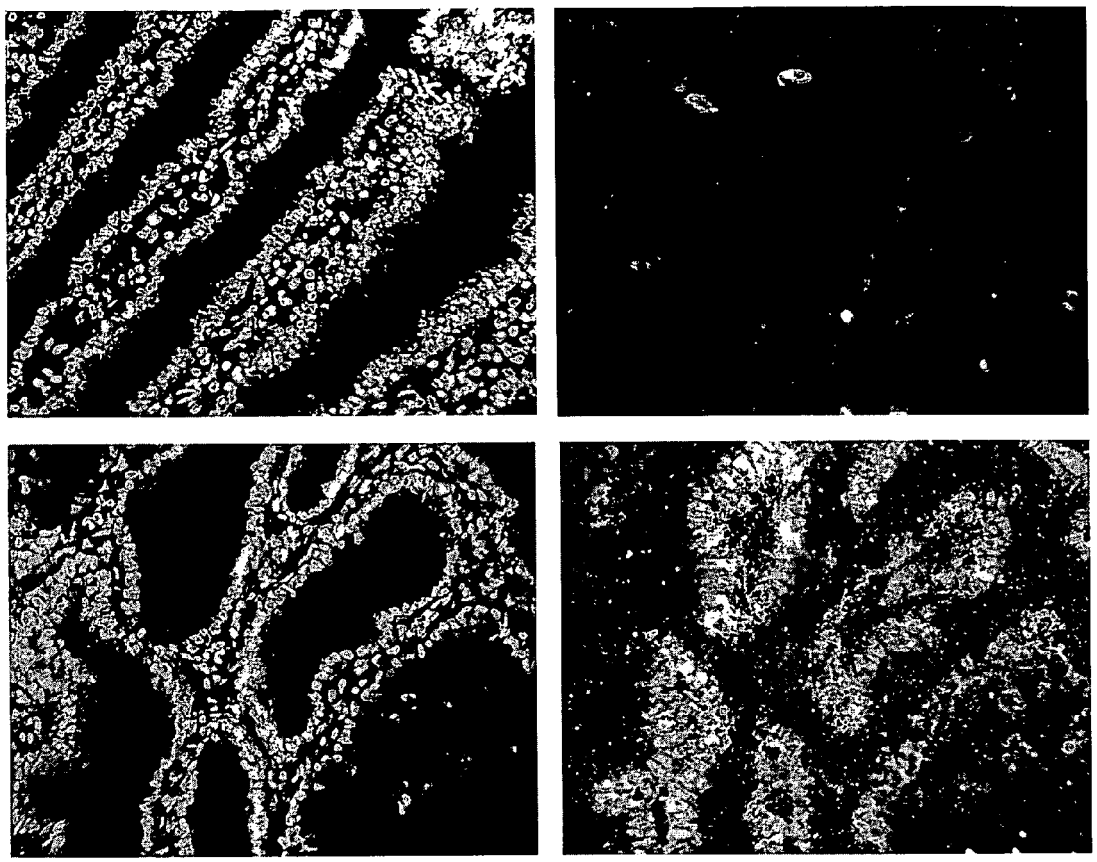

FIG. 3: Uptake of STxB by intestinal tumors after 24 h, comparison with normal tissue. Upper panels: normal duodenum. Lower panels: tumor from the periampullar region. Left panels: nuclei are stained with Hoechst dye. Right panels: anti-STxB staining.

Figure 4:
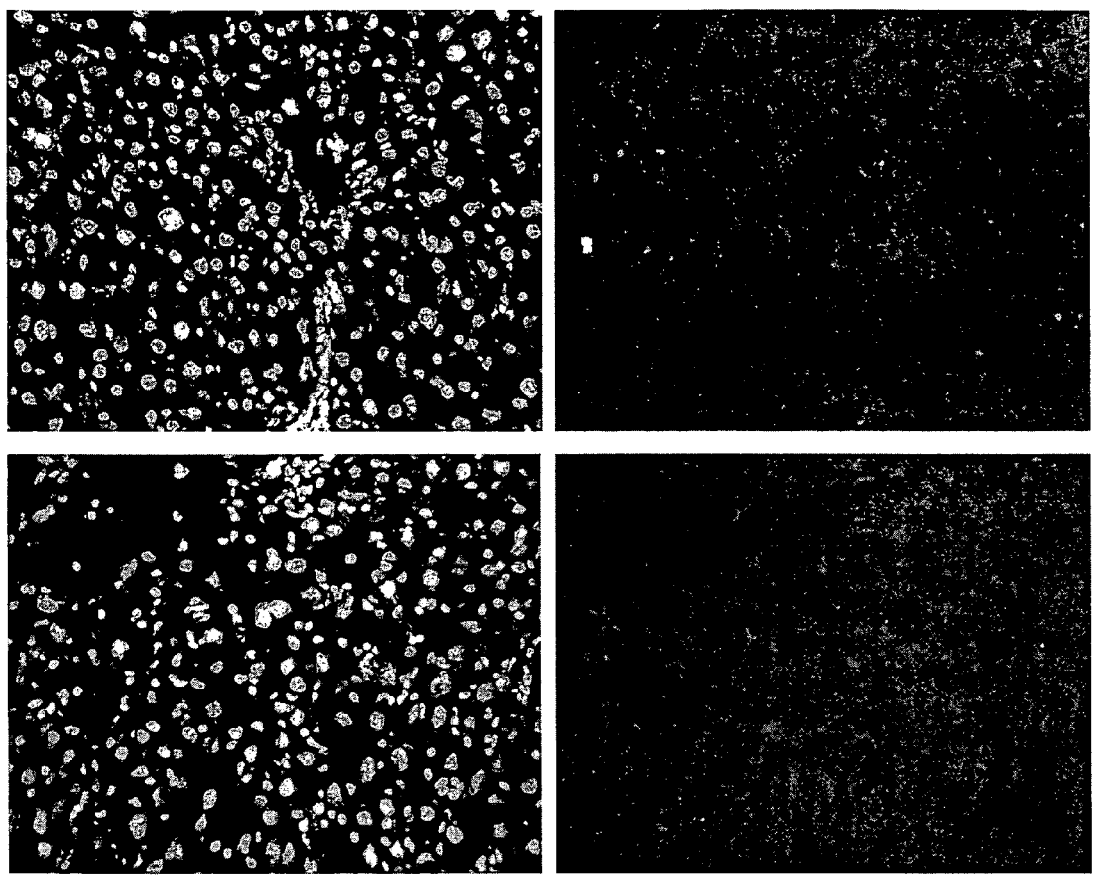

FIG. 4: STxB is not present in control tissue (liver), even after 24 h. Upper panels: a non-treated control animal. Lower panels: animal treated with STxB after 24 h incubation. Left panels: nuclear staining (Hoechst), right panels: anti-STxB staining.

Figure 5:
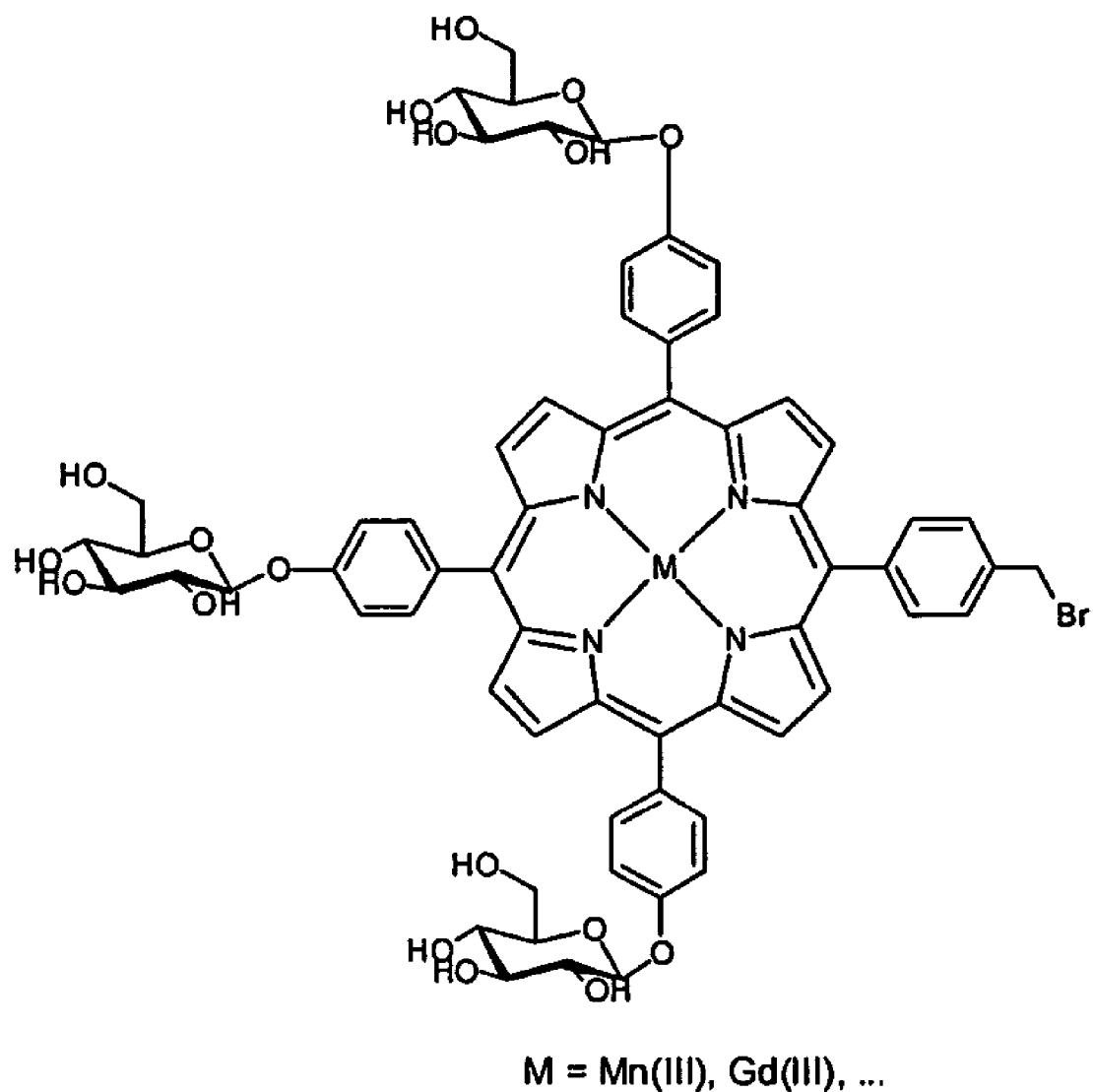

FIG. 5: Structure of the water-soluble metallo-porphyrin that is coupled to STxB/Cys.

Figure 6:
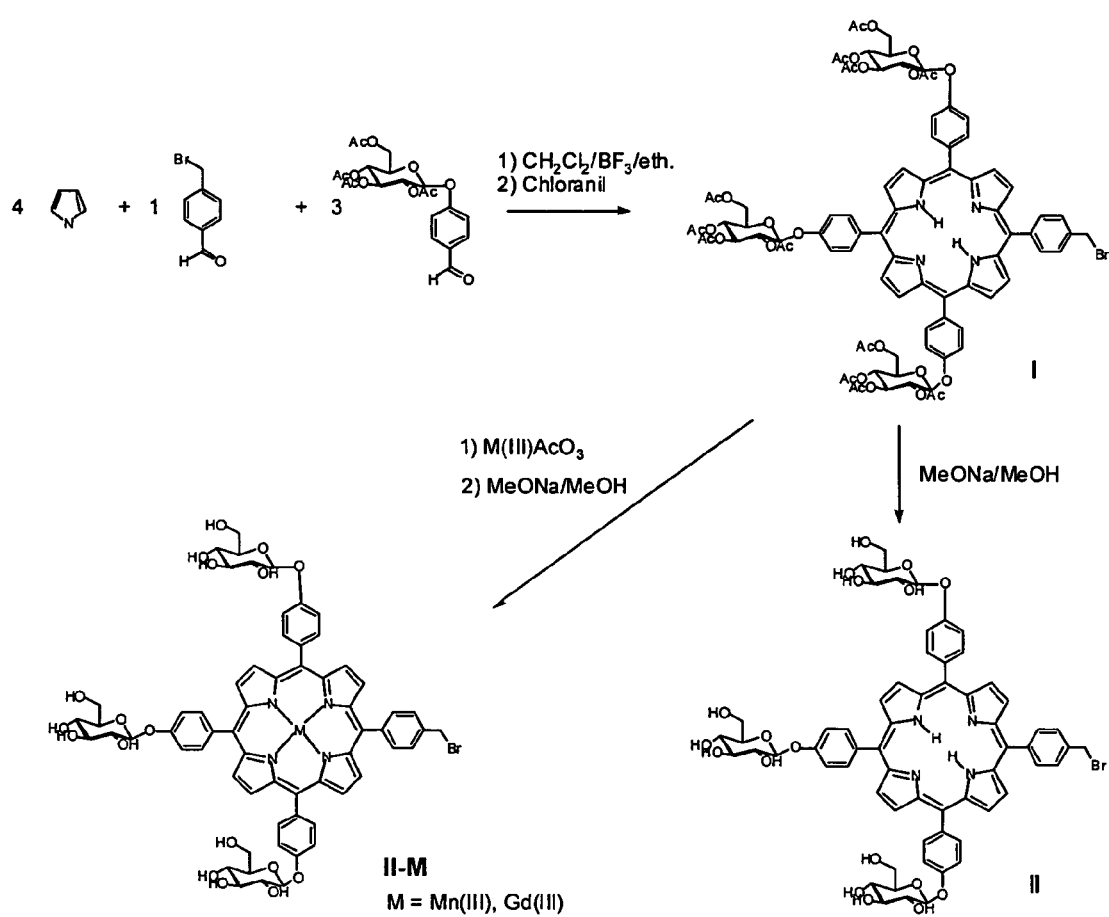

FIG. 6: Synthesis of compounds that are coupled to STxB/Cys to function as a contrast agents in RMI (II-M) or as an anti-tumor cytotoxic drugs for PDT (II).

Figure 7:
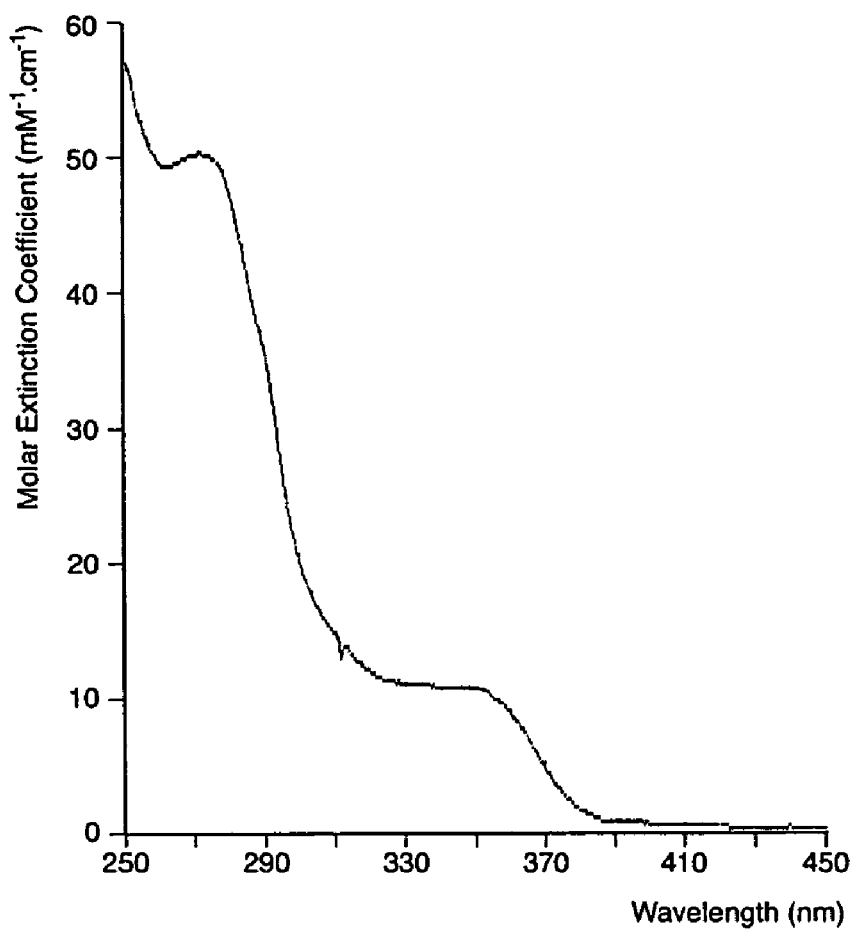

FIG. 7: Optical absorption spectrum of holo-NCS/STxB after incorporation of $NCS_{Chrom}$ and filtration over sephadex G25 to remove excess, non-specifically bound $NCS_{Chrom}$.

FIG. 8: Summary of the effect of low temperature (0° C.) and PPMP on the response of HeLa cells to 4 nM (relative to $NCS_{Chrom}$) holo-NCS or holo-NCS/STxB. Blanks are treated on ice for control.

FIG. 9: Scheme of MBS coupling method.

FIG. 10: Overexpression of $Gb_3$ by murine and human tumors. (A) STxB overlay experiment on neutral GSL extracted from normal (Ctrl) and tumor tissue samples obtained from Ras-APC mice. (B) Quantification of $Gb_3$ expression in normal (white bars) or tumor (grey bars) intestinal tissue samples. The averages are shown in black bars. (C) STxB overlay experiment on neutral GSL extracted from normal human colon (Ctrl) and tumor tissue. (D) Representation of $Gb_3$ overexpression by human colon tumors. Results are expressed as the ratio of $Gb_3$ expression in tumors over $Gb_3$ expression in normal adjacent tissue obtained from the same patient. Six independent experiments (white bars) and their average (black bar) are represented.

FIG. 11: Tumor imaging using multiphoton microscopy. (A, B, C) Appearance of untreated intestinal tissue, revealed by autofluorescence on un-fixed, unstained tissue. (A) Villi in the duodenum. (B) Aligned epithelial cells in normal tissue. (C) Staggered cells with enlarged nuclei in dedifferentiated tumor. (D, E) Gavage experiment with Cy5-STxB. Tumor tissue is brightly labeled, while the surrounding normal tissue appears dark, due to reduced excitation regimes, when compared to (A-C).

FIG. 12: Vectorization of glyco-porphyrin H2TPP(p-O-b-D-GluOAc)3 (p-CH2Br) to cancer cells. The upper blue line (open squares) reports the response of Hela cells in which the expression of Gb3 was inhibited using PPMP. The lower red line (open circles) reports on control HeLa cells. Note that the survival is significantly affected only in HeLa cells in which Gb3 is expressed, showing the receptor-dependent delivery of the glyco-porphyrin H2TPP(p-O-b-D-GluOAc)3(p-CH2Br) to cancer cells, via STxB.

FIG. 13: Analysis of STxB-dependent β-GUS targeting to the retrograde route of cancers cells. Note the perfect overlay of the labeling (yellow, lowest panel) obtained with the antibodies directed against STxB (red, uppermost panel) and β-GUS (green, middle panel).

FIG. 14: Vectorizartion of β-GUS activity onto cancer cells. β-GUS activity is given in arbitrary units. Note that Gb3 expressing HeLa cells (Gb3+ cells) show a significant increase of β-GUS activity comparatively to non-expressing cells (Gb3- cells). The activity of purified β-GUS is shown as a control.

FIG. 15: Computed quantitative T2 map of the four cell preparations. Note that cells with which NP have associated appear dark. Non-coated NP readily and non-specifically bind to HeLa cells. BSA-coating (NP-BSA) reduces non-specific binding. STxB-functionalized NP (STxB-Cys-MBS-BSA-NP) bind to HeLa cells in a receptor dependent manner.

FIG. 16: Targeting of STxB-EDEKKK (EDEKKK is SEQ ID NO: 2) coupled biotin to the Golgi apparatus of HeLa cells. Biotin is coupled to STxB-EDEKKK (EDEKKK is SEQ ID NO: 2) according to the manufacturer instructions (Pierce). After binding to HeLa cells on ice (30 min), STxB-EDEKKK (EDEKKK is SEQ ID NO: 2) is internalized for 45 min at 37° C. The cells are fixed, and double-stained for STxB (13C4 antibody) and streptavidin to detect vectorized biotin. Note that vectorized biotin accumulates in the perinuclear Golgi apparatus.

EXAMPLE 1

Validation of the Mouse Model for in Vivo Diagnostic and Therapeutic Administration of Hybrid Compounds The murine model bears a colorectal cancer.

Pilot experiments were performed to examine the tissue distribution of STxB at 2.5 hours or 24 hours post-injection. The STxB is taken up extensively in the tumoral tissue, but not in normal intestinal epithelium, which expresses low levels of $Gb_3$. Since the STxB is non-toxic, this procedure can be applied repeatedly for longitudinal studies of tumor development or tumor regression upon treatment.

1.1: $Gb_3$ is Strongly Over-expressed in Intestinal Tumors: Overlay Analysis

Three genetically modified mouse models for colorectal cancer are used, and they show essentially the same results in this study. We use transgenic animals that express oncogenic Ras under control of the villin promoter in intestinal epithelium, with the genetic background B6D2 (Tg villin-K-ras V12G; (Janssen et al., 2002) and the mouse line $Apc^{1638N}$ that carries a heterozygous mutated allele of the Apc (*adenomatous polyposis coli*) locus in the C57BI/6 background (Fodde et al., 1994). Furthermore, a double transgenic line RasAPC is created by crossing the two transgenic lines. The animals used have an age of >6 months and a weight of 25-35 grams at the time of injection. The mice are maintained under a 12 hour light-dark cycle and fed with standard diet and water ad libitum.

Intestinal specimens are processed immediately after sacrificing the animal. Small and large intestines are opened longitudinally, tumorous regions are dissected together with surrounding normal tissue and either embedded for cryosections (see below), or fixed in AFA (75% ethanol, 20% formalin, and 5% acetic acid) for 24 hours. After embedding, three μm thick sections are cut from the tissue blocks, dewaxed, rehydrated and processed by routine H&E staining. Tumors are classified and graded according to the World Health Organization classification of tumors (Hamilton and Aaltonen, 2000). Adenocarcinomas are considered invasive if malignant epithelial cells, arranged in glandular and/or trabecular structures, are found invading at least the submucosa.

Lipid extraction is done according to the method of Bligh and Dyer (Bligh and Dyer, 1959). Human and mouse tumor tissue and adjacent non-tumoral specimen are weighted, mechanically homogenized in 1 ml of aqueous buffer and injeceted into 3.75 ml of chimoroform:methanol (1:2).

After mixing, 1.25 ml of chloroform and 1.25 ml of water are added. Phases are separated after mixing, and the hydro-alcoholic phase is washed once with 1.5 ml of chloroform. The combined chloroform phases are dried under nitrogen, and lipids are saponified at 56° C. for 1 hour in 1 ml of methanol/KOH. The saponification reaction is once again extracted as described above, and the chloroform phase are washed once with methanol:water (1:1). The isolated neutral glycolipids are spotted on high performance-TLC plates (Merck, Darmstadt, Germany) and separated with chloroform:methanol:water (65:25:4). Dried plates are soaked in 0.1% polyisobutylmetacrylate in hexane, floated for 1 hour in blocking solution, followed by incubation with STxB (20 nM), primary polyclonal anti-STxB and secondary horse radish peroxidase- or alkaline phosphatase-coupled anti-rabbit antibodies. Reactive bands are revealed using enhanced chemiluminescence or chemifluorescence (Amersham Pharmacia, Little Chalfont, UK) and PhosphorImager.

$Gb_3$ expression levels are compared between normal and tumor tissue.

Figure 10:
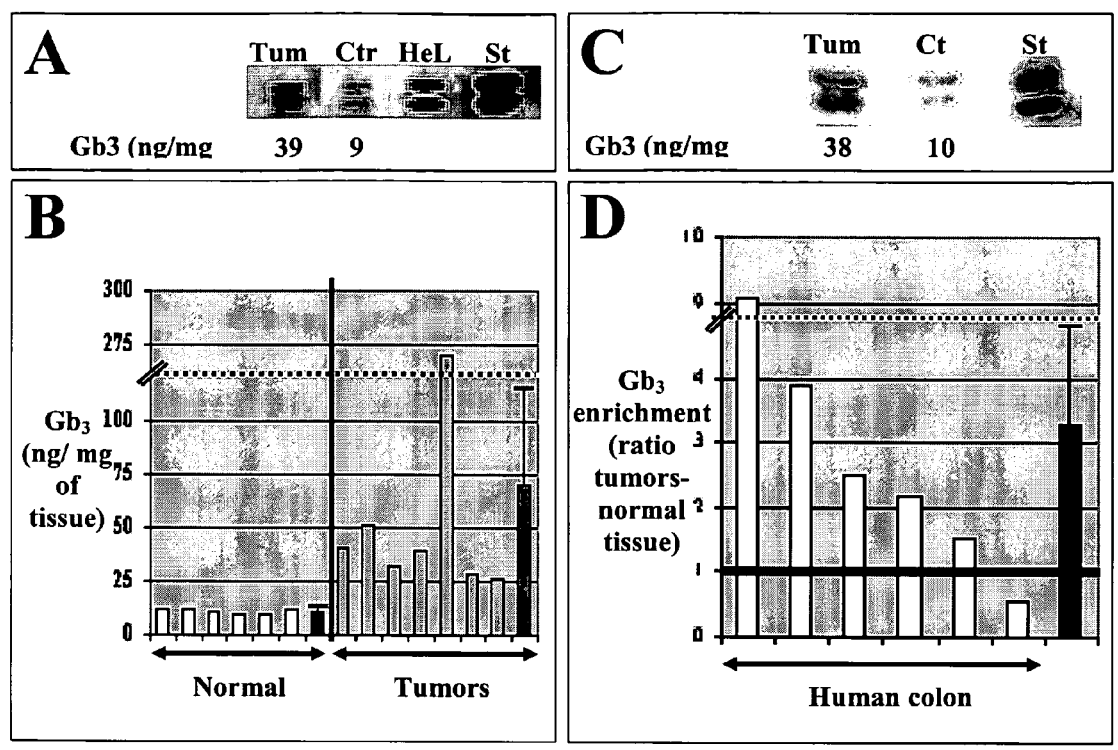

FIG. 10 shows overexpression of $Gb_3$ by murine and human tumors 1.2: $Gb_3$ is Strongly Over-expressed in Intestinal Tumors: STxB-Cy3 Labelling on Tissue Sections STxB-Cy3 labeling of cryosections is carried out to detect endogenous $Gb_3$ in normal intestinal and tumor tissue of otherwise untreated animals. A stock solution of STxB-Cy3 (0.22 mg/ml) is diluted 22 fold in PBS+0.2% BSA (final concentration 10 µg/ml), and is incubated on sections for 30 min either before or after PFA fixation at room temperature for 20 min. Subsequently, the paraformaldehyde-fixed sections are treated with 50 mM $NH_4Cl$ in PBS for 20 min, and solubilized with 0.1% Triton X-100 for 5 min. Counterstaining with FITC-phalloidin and Hoechst dye as described above. Normal tissue is overall negative, except for a faint staining that was sometimes observable in the crypts, and occasional staining of single cells within the normal tissue. These cells may constitute enteroendocrine/lymphatic cells, based on morphological criteria. In contrast, tumors are strongly stained.

1.3: Orally Administered STxB Reaches Intestinal Tumors in Vivo

A pilot experiment is undertaken with a color marker to follow the distribution of injected fluid in the murine intestine: 0.5 ml of trypan blue is injected. The animal is sacrificed after 45 min, and the intestinal tract is removed and analyzed for distribution of trypan blue. The blue staining has clearly progressed through the largest part of the small intestine.

Two animals are then injected with STxB, using in one animal a dose of 0.5 ml of a 1 mg/ml solution (animal A), or a smaller dose of 0.5 ml of a 0.1 mg/ml solution (animal B). A flexible plastic needle with a length of 40 mm and a diameter of 0.4 mm is used (Marquat Genie Biomedical, Boissy St Leger, Reference V010440). STxB is purified from bacteria (Mallard and Johannes, 2002) and dialyzed against PBS before injection. Animals are injected in the oesophagus with a single dose of 0.5 ml of a solution of varying concentrations STxB in PBS without anaesthesis. After the force-feeding, animals are kept for various time points and are allowed to feed with standard diet and water ad libitum.

At 2.5 hours post-injection, the mice are sacrificed by cervical dislocation and tissues are removed for subsequent analyses. Tissue samples are taken along the intestinal tract, as well as tumors from each animal. The resected normal and tumoral tissue are prepared for cryosections, or processed for lipid extraction and subsequent overlay experiments, as described above. Animals are analyzed on serial cryosections with the monoclonal as well as the polyclonal antibodies for STxB. Mouse tissues embedded in Tissue-tek OCT (Sakura) are cut in serial sections at 5 µm thickness, air dried, and fixed with 3% paraformaldehyde at room temperature for 20 min. The paraformaldehyde-fixed sections are treated with 50 mM $NH_4Cl$ in PBS for 20 min, and solubilized with 0.1% Triton X-100 for 5 min. Antibodies used are: monoclonal and polyclonal antibodies specific for STxB, diluted 1/100 (Falguières et al., 2001), mAb anti-Villin ID2C3 (Dudouet et al., 1987), anti-Ki67 pAb (Novocastra), polyclonal antiserum anti-chromogranin A/B (ProGen, Heidelberg), secondary antibodies were goat anti-mouse IgG and goat anti-rabbit IgG coupled to Alexa488 or Cy3 (Jackson Immunoresearch), TRITC-phalloidin (Sigma) to visualize actin, and the dye Hoechst 33258 (Sigma) to stain nuclei.

Tumoral regions are identified by standard histological criteria, and they are positive for the proliferative marker Ki67. Epithelial cells are identified with a monoclonal anti-villin antibody. No STxB staining is observable in normal intestinal epithelial cells (FIG. 1), but strong staining occurrs in some occasional single cells that are interspersed in the epithelial layer, and present morphological characteristics of enteroendocrine cells, and are found to be positive for chromogranin A/B staining, a marker of enteroendocrine cells (FIG. 2). Furthermore, a few cells are labeled that might be of lymphatic origin (macrophages or dendritic cells). This staining pattern is found in the duodenum, jejunum, and ileum, but is absent from the colon. Peyer's patches are also essentially unmarked. A periampullar adenocarcinoma from animal A is very strongly labeled (FIG. 1). The labeling comprises about 50% of the whole tumor surface area, and is found in epithelial cells lining trabecular or glandular structures. Furthermore, stromal regions with signs of inflammation sometimes show staining, labeled cells are of putative lymphoid origin. The stroma is otherwise negative. However, two different lesions from the same animal are negative, apart from the staining in cells of putative lymphoid origin in the stroma. The animal B receives the weaker dose of STxB and shows essentially the same results, normal tissue is negative with the exception of a few single cells. A periampullar tumor is not marked, but a second tumor from the duodenum is labeled in tumor cells of epithelial origin (as evidenced by anti-villin staining). However, the overall intensity of the staining is markedly decreased as compared to animal A (dosis of 1.0 mg/ml).

1.4: STxB is Retained in the Tumors After an Incubation Period of 24 h

Two animals are injected with 0.35 ml of a 1 mg/ml solution of STxB in PBS. The mice are sacrificed after 24 hours. Tissue samples are taken from control tissue (liver), and the intestinal tract: duodenum, jejunum, ileum, proximal colon. Tumors are isolated from both animals, and prepared for cryosections, and stained with polyclonal Ab anti-STxB and anti-chromogranin A/B. Even after 24 hours, STxB is still detectable in occasional cells in the otherwise negative epithelium, and is still very strongly present in tumors (FIG. 3). No staining is observable in liver sections from both animals (FIG. 4).

EXAMPLE 2

In Vivo Diagnostic by MRI 2.1: Synthesis and Coupling of Porphyrin (Contrast Agent) to STxB-Cys A contrast agent that is commonly used for RMI studies are paramagnetic metalloporphyrins. To target a hydrophilic porphrin to tumor cells, the following substance is synthesized.

The porphyrin I (FIG. 6) is prepared by condensation of pyrrole, para-2,3,4,6-tetraacetyl glucosyloxy benzaldehyde (Halazy et al., 1990) and -bromo- para-tolualdehyde (Wen et al., 1997) in high yield (31%) by Lindsey's method (Lindsey et al., 1987). Compound I is purified by silica gel preparative thin layer chromatography eluted by a mixture of methylene chloride/acetone (10/1, v/v) and characterized by physical methods. Microanalysis for $C_{87}H_{85}BrN_4O_{30,}$ 3 $H_2O$ C, 58.03; H, 5.09; N, 5.09 found C, 58.07; H, 4.77; N, 2.74, UV-visible spectrum in methylene chloride $_{\chi max}$ (nm), (ϵm-mole$^{-1}$ cm$^{-1}$) 419.5 (414.3), 516 (17.9), 552 (10.5), 591 (6.9), 647 (5.9), $^1$H NMR spectrum in $CDCl_3$ δ (ppm) 8.88 (s, 8 H, pyrrole), 8.26 (d, 2 H, ortho-phenyl), 8.16 (d, 6 H, ortho-phenoxy), 7.82 (d, 2 H, meta-phenyl), 7.42 (d, 6 H, meta-phenoxy), 5.50 (m, 9 H, H "ose"), 5.33 (m, 3 H, H "ose"), 4.88 (s, 2 H, $CH_2Br$), 4.45 (dd, 3 H, $HC_{6a}$ "ose"), 4.33 (d, 3 H, $HC_{6a}$ "ose"), 4.08 (m, 3 H, $HC_5$ "ose"), 2.24 (s, 9 H, acetyl), 2.14 (s, 9 H, acetyl), 2.13 (s, 18 H, acetyl), −2.79 (s, 2 H, NH). Glycoconjugated compound II (FIG. 6) is obtained quantitatively from I by treatment with MeONa/MeOH (Zemplén, 1927). UV-visible spectrum in DMSO $_{\chi max}$ (nm), (ϵ mmole$^{-1}$ cm$^{-1}$) 422 (373.7), 517.5 (16.2), 554 (11.5), 592.5 (6.7), 649 (6.6), $^1$H NMR spectrum in DMSO $d_6$ δ (ppm) 8.87 (s, 6 H, pyrrole), 8.82 (s, 2 H, pyrrole), 8.24 (d, 2 H, ortho-phenyl, J=7.9 Hz), 8.13 (d, 6 H ortho-phenoxy, J=7.9 Hz), 7.89 (d, 2 H, meta-phenyl, J=8.3 Hz), 7.48 (d, 6 H, meta-phenoxy, J=8 Hz), 5.7 (s, 2 H, $CH_2Br$), 5.23 (d, 3 H, $HC_1$ "ose"), 3.82 (d broad, 3 H, $HC_{6a}$ "ose"), 3.54 (m, 3 H, $HC_{6a}$ "ose"), 3.42 (m, 3 H, $HC_3$ "ose"), −2.91 (s, 2 H, NH), $^{13}$C NMR spectrum in DMSO $d_6$ δ (ppm) 157.4 (para-C phenoxy), 141 (meso-Cphenyl), 137 (para-C phenyl), 135.1 (meso-C and meta-C phenoxy), 134.5 (ortho-C phenyl), 131 (C—H pyrrole), 127 (meta-C phenyl), 120 (meso-C) 114.3 (ortho-C or meta-C phenoxy), 100.5 ($C_1$ "ose"), 73.5 ($C_2$ "ose"), 60.7 ($C_6$ "ose"), 45.7 ($CH_2Br$), MALDI-TOF Calc; for $C_{63}H_{61}BrN_4O_{18}$1240.32, found M+1 1241.48.

For coupling of compound II or II-M to STxB/Cys, 3 mg/ml of STxB/Cys in 10 mM borate pH 9.0, 75 mM NaCl, 50% DMSO is incubated for 2 hours at room temperature with a 5-fold excess of compound II or II-M. Coupling is verified by MALDI-TOF, and coupled protein is purified by gel filtration and stored at −80° C.

2.2: Coupling of BSA to STxB/Cys and Binding to Nanoparticles (or Ferrofluid; Contrast Agent)

20 mg/ml of purified bovine serum albumine (BSA) in 100 mM HEPES, pH 7.4, is incubated with 1 mM of the heterobifunctional cross linker MBS for 30 min at room temperature. The reaction is passed through a PBS/EDTA 10 mM equilibrated gel filtration column. Eluted BSA is concentrated to 20 mg/ml. 1 volume of STxB/Cys at 3.5 mg/ml in PBS/EDTA is mixed with 1 volume of activated BSA and incubated over night at room temperature. The coupling product is purified by passage over an anti-STxB immunopurification column and a MonoQ anion exchange column. According to Western analysis, the product is essentially pure. Binding of STxB/Cys-BSA to nanoparticles is done as described (Wilhelm et al., 2002).

2.3: Non-invasive Imaging of $Gb_3$ Distribution Principle

Monitoring of $Gb_3$ distribution by MRI techniques requires administration of a compound composed of the receptor specific molecule, STxB, linked to an appropriate paramagnetic contrast agent (ferrofluid or porphyrin). Accumulation of this targeted contrast agent at the fixation site locally modifies the water relaxation rates R1,R2,R2* leading to MRI signal modification using T1 and/or T2 and/or T2* weighted imaging sequences. Significant signal difference in images acquired before and after administration of the contrast agent depicts the regions of $Gb_3$ over-expression when non-specific accumulation can be excluded. The protocol can be applied to different tumor types over-expressing $Gb_3$. The typical measuring procedure described hereafter is optimized for imaging intestinal tumors developed by our transgenic mouse model.

Image Acquisition

Tumors are first detected by MRI in a screening session without contrast agent administration. Imaging is performed on a high field mini-imaging system, in our case a Bruker Biospec 47/30 system equipped with a 4.7 Tesla horizontal magnet. For that, the mouse is anaesthetized (preferred anaesthetic: isoflurane) and placed in a cradle in supine position. Tubes containing circulating warm water are placed close to the animal in order to maintain body temperature. The animal is introduced in an MRI probe adapted to the size of the animal. Our preferred probe is a home-made slotted cylinder type probe (d=44 mm). A tube containing a water solution with adjusted R1/R2 relaxation rates is also introduced into the MRI probe and serves as an external signal intensity reference. Respiratory triggering has to be performed in order to obtain images of the abdominal region with minimal motion artifacts Several approaches for respiratory triggering in the mouse exist. Our preferred high sensitivity triggering device is home-made and is based on an inflatable chamber placed on the mouse abdomen and connected to a pressure transducer which delivers the trigger signal via appropriate electronics to the MRI system. Tumor detection is performed by means of a 3D T2 weighted fast spin echo imaging sequence with a field of view covering typically the liver and the intestinal region. Under these conditions tumors appear as hypersignal regions. The image resolution is typically 0.1×0.1×0.5 $mm^3$. Tumors are localized with respect to anatomical markers, for example the stomach—intestine junction. Tumors are then imaged with T1 and T2* weighted fast gradient echo sequences. This terminates the first imaging session.

The second imaging session is performed on the same mouse after administration of the contrast agent (preferred administration: oral). The imaging protocol matches exactly that of the first imaging session.

Image Analysis

Regions of interest (ROIs) covering the tumors are defined on co-localized slices from the two imaging sessions. Mean intensities of the ROIs are measured and normalized with respect to intensity of the external reference. Significantly different signal intensity detected in tumors after contrast agent administration demonstrates therefore $Gb_3$ over-expression.

2.4 Additional RMI Experiment

MRI is performed on pellets of HeLa cells (about 50×10$^6$ cells/pellet) obtained after incubation with iron oxide nanoparticle based contrast agents (nanoparticles, NP) and subsequent centrifugation in Eppendorf tubes. More precisely, cell sample preparation comprised the following main steps: 1. Incubation of cells and NP at 4° C. for 30 min. (binding); 2. washing (3 times); 3. incubation at 37° C. for 2 hours (endocytosis); 4. washing (3 times); 6. centrifugation. Four different conditions were used: 1. Incubation with untreated iron oxide nanoparticles (NP); 2. incubation with BSA coated nanoparticles (NP-BSA); 3. incubation with the targeted contrast agent, i.e. NP-BSA linked to STxB (STxB-Cys-MBS-BSA-NP); 4. same condition as (3.) with PPMP treated cells to reduce $Gb_3$ expression.

For MR imaging at 4.7 Tesla, cell samples were positioned in a sample holder allowing simultaneous imaging of the four samples. Quantitative T2 relaxation time (=inverse of relaxation rate R2) measurements were performed using a single-slice multi-echo MRI sequence (10 echos, echo times ranging from 4.5 msec to 45 msec).

Figure 15:
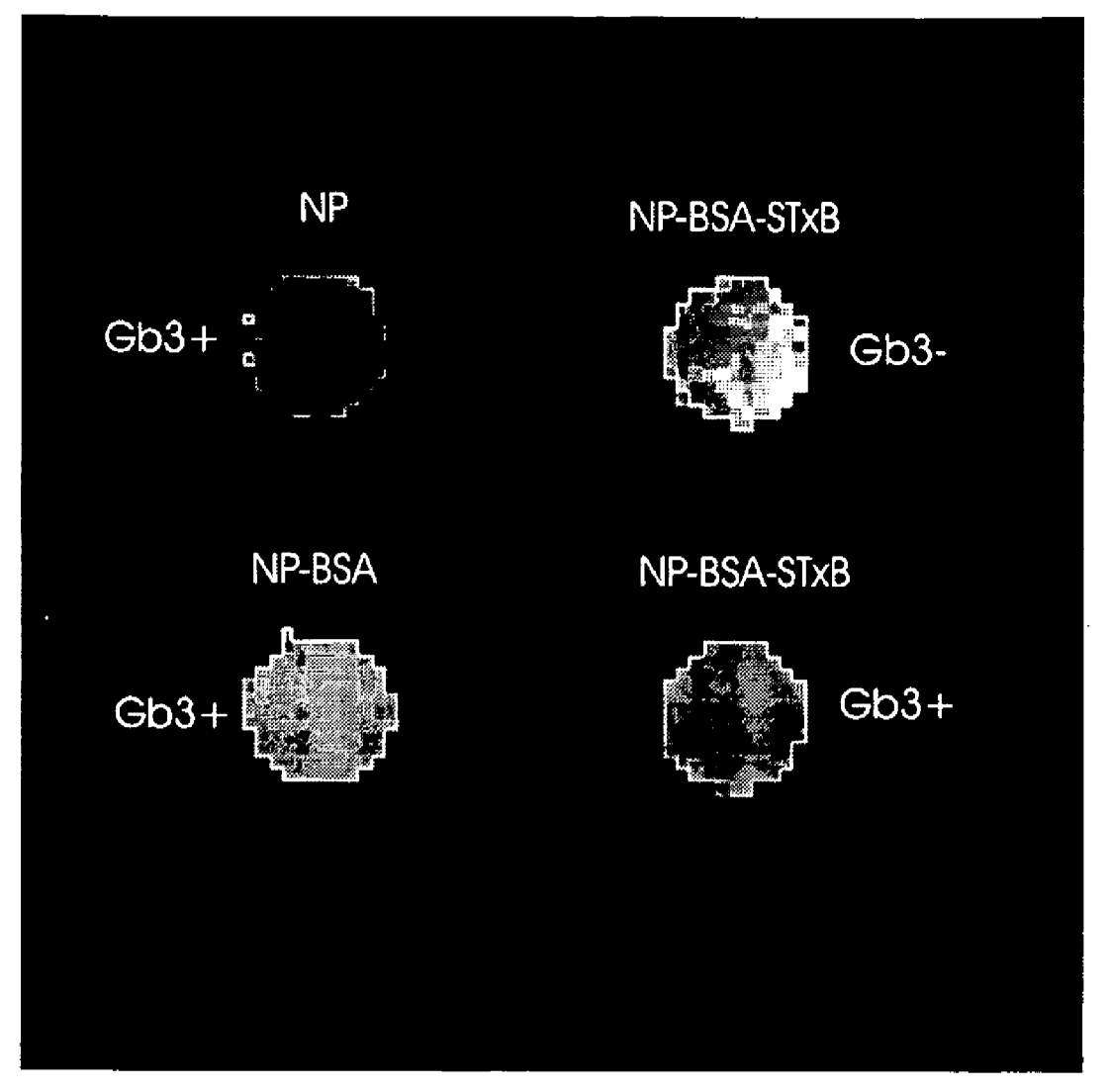

The results are illustrated on FIG. 15.

EXAMPLE 3

Tumor Imaging Using Multiphoton Microscopy

Method:

Resected tumoral tissu samples from villin-RasV12 mice are placed directly into an imaging chamber containing Dulbecco's modified Eagle's medium (DMEM) without phenol red. We use an IX70 inverted Olympus microscope. A tunable pulsed Ti: Sapphire laser (Tsunami; Spectra Physics) pumped by a Nd-YVO4 laser (Milennia, Spectra Physics) provides 70 fs pulses at 750 nm with a 80 MHz repetition. Fluorescence is detected with the built-in Fluoview photomultiplier (R928, Hamamatsu Photonics) in the descanned configuration.

Figure 11:
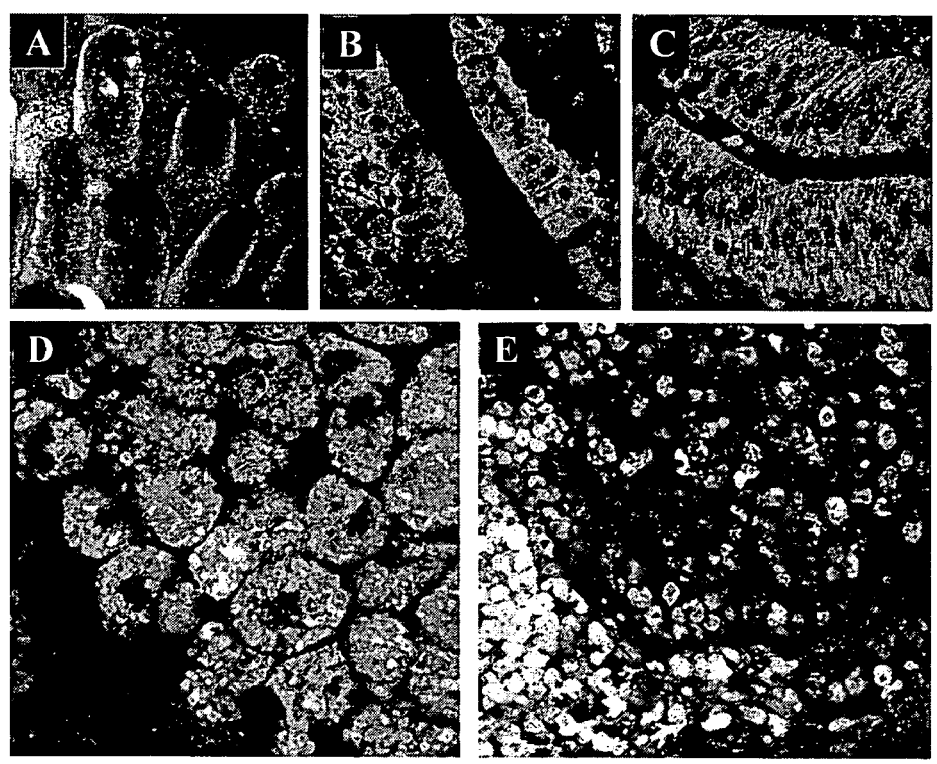

Functionalized STxB can be used to target and identify intestinal tumors by non-invasive in-depth imaging approaches. The fluorophore Cy3, when coupled to STxB, is strongly accumulated in intestinal tumors, demonstrating that STxB delivers contrast agents for in vivo diagnostics to Gb3-expressing tumors. We show this using optical biopsy capacity of multiphoton imaging. First at all, villi of the duodenum of resected normal or cancerous tissue are observed without prior fixation or staining, using non-linear autofluorescence (FIG. 11 A-C). The regular alignment of nuclei (dark zones) in the epithelial cells is clearly visible (FIG. 11 B). In contrast, nuclei appear enlarged and staggered in the de-differentiated tumor sample (FIG. 11 C). Transgenic mice are then force-fed with fluorophore-coupled STxB. After 6 hours, tumor samples as well as samples of normal mucosa are resected and observed by multiphoton imaging. Normal tissue appears dark, while tumor tissue is brightly labeled with internalized STxB (FIG. 11 D-E).

The results are illustrated on FIG. 11.

EXAMPLE 4

Tumor Treatment by Dynamic Phototherapy

Method:

The glycoporphyrin H2TPP(p-O-b-D-GluOAc)3(p-CH2Br) is dissolved in DMSO at 0.7 mM and mixed with an equal volume of STxB-Cys at 5.3 mg/ml. The mixture is incubated for 2 hours at room temperature and then passed through an G25 gel filtration column. The coupling product is snap frozen in liquid nitrogen and kept at −80° C. for storage.

Human tumor cells (either HT29 colon carcinoma or Hela cervix adenocarcinoma) are cultivated in Dulbecco's MEM supplemented with 10% fetal calf serum (FCS). Cells from log-phase culture are seeded in 96-microwell plates (0.2 mL–3×10⁴ cells/well) and kept at 37° C. in a water-jacketed incubator for 3 hour under an air/$CO_2$ atmosphere (5% $CO_2$). Tested compounds are added under the minimum volume. Plates are incubated 3 hours, then medium is removed and cells are washed twice with phosphate buffered saline (PBS) before addition of fresh medium free of drug. Irradiation with visible light ($2J/cm^2$) is performed through the bottom of the plates using a home made "light box" fitted with an orange filter (0% T at 520 nm and 80% T at 590 nm and above) leading to a fluence of 2 $mW/cm^2$. Plates are incubated for three days before evaluation of the cell survival using the MTT assay (Mosmann, 1983) using 30 min incubation with 10 μg/well of 3-[4,5-dimethylthiazol-2-yl]-2,5-diphenyl tetrazolium bromide (MTT, Sigma). After removal of the medium, formazan crystals are taken up with 100 μL of DMSO and absorbance at 540 nm are measured with a Bio-Rad microplate reader (Model 450). Survival is expressed as % of untreated controls.

Comparison between treatment with free porphyrin or with STxB-porphyrin conjugate either on HeLa-$Gb_3^+$ cells, HT29 cells (with low expression of $Gb_3$) or fully $Gb_3$ expression inhibited HeLa cells allows to verify the specific dye targeting by STxB.

The results are illustrated on FIG. 12.

EXAMPLE 5

Tumor Treatment by Neocarzinostatin a) Purification of Neocarzinostatin

Holo-NCS is purchased from Nippon Kayaku Co. (Tokyo, Japan) and purified as described (Favaudon, 1983). Purified holo-NCS is dialyzed against distilled water acidified with 1 mM acetic acid, lyophilized to dryness and stored in the dark at −80° C.

The holo-NCS preparation is ≧98% pure from isoelectric focusing (pH 2.5-4.5 gradient) on polyacrylamide gel and free from contaminating apo-NCS from absorption and fluorescence spectrocopy. $NCS_{Chrom}$ is mostly (>90%) in "A" form according to the nomenclature of Napier et al. (Napier et al., 1981).

Holo-NCS solutions are titrated by absorption spectrophotometry using the molar extinction coefficients, namely, $\epsilon_{277} = 14.4$ $mM^{-1}.cm^{-1}$ for apo-NCS and, for holo-NCS, $\epsilon_{273} = 35.4$ $mM^{-1}.cm^{-1}$ and $\epsilon_{340} = 10.9$ $mM^{-1}.cm^{-1}$.

b) Coupling of Apo-NCS to STxB-Cys 20 mg/ml of purified apo-NCS in 100 mM HEPES, pH 7.4, is incubated with 1 mM of the heterobifunctional cross linker MBS for 30 min at room temperature. The reaction is passed through a gel filtration column equilibrated with PBS containing 10 mM EDTA. Eluted activated apo-NCS is concentrated to 20 mg/ml. One volume of STxB/Cys at 3.5 mg/ml in PBS/EDTA is mixed with 1 volume of activated apo-NCS and incubated over night at room temperature. The coupling product is purified by passage over an anti-STxB immunoprufication column and a gel filtration column. According to Western analysis, the coupling product, termed apo-NCS/STxB is essentially pure.

c) Incorporation of $NCS_{Chrom}$ into the Apo-NCS/STxB Conjugate

1 μmole of lyophilized holo-NCS powder (11.3 mg dry weight) is suspended in 1 ml anhydrous, ice-cold methanol acidified with 1 N HCl, and incubated for 10 min with vortexing every 2 min followed by centrifugation (10 min at 11,000 g). The supernatant fraction containing free $NCS_{Chrom}$ is recovered and titrated by absorption spectrometry as described (Favaudon, 1983). The whole procedure is performed at ice temperature in the dark. The yield of $NCS_{Chrom}$ extraction is close to 50%.

Six nmole of the apo-NCS/STxB conjugate in 1 ml PBS buffer, pH 7.4 are cooled in ice and mixed under vortexing with a 10-fold molar excess of $NCS_{Chrom}$ from the above preparation. A precipitate is formed, due likely to the acid pH or to the low solubility of free $NCS_{Chrom}$ in aqueous medium. The preparation is centrifuged (10 min, 11,000 g). The supernatant fraction is loaded onto a 1.0×20 cm column of Sephadex G-25 equilibrated with 20 mM phosphate buffer, pH 6.4. The pellet is redissolved in 500 µl of the same buffer, and pooled on the column with the first, supernatant fraction. Elution is performed in 20 mM phosphate buffer, pH 6.4. All operations are performed in the dark at 4° C. The collected fractions are checked by absorption spectrophotometry; fractions containing protein (detected by an absorbance at 280 nm) present an absorption band centered at 340 nm, typical of protein-bound $NCS_{Chrom}$ (FIG. 7).

The protein fractions are pooled, concentrated by centrifugation over a Centricon® centrifugal filter unit (3.000 Da cutoff), sterilized by filtration over a Millex®) unit (0.2 µm pore size) and stored in the dark at liquid nitrogen temperature (for prolonged storage it is recommended to lower the pH down to pH 5.0). The final concentration of the reconstituted holo-NCS/STxB is 9.8 µM relative to the absorption of protein-bound $NCS_{Chrom}$ at 340 nm.

d) Cytotoxicity Assays

Human cervix adenocarcinoma HeLa cells are maintained as exponentially growing monolayers in Dulbecco modified Eagle's minimum essential medium with 4.5 g/l glucose, 0.1 g/l pyruvate, $10^5$ UI/l penicilline, 0.1 g/l streptomycine, 0.86 g/l Glutamax I and 10% v/v foetal calf serum (37° C., 5% $CO_2$), without or with 5 µM DL-threo-1-phenyl-2-hexadecanoyl-amino-3-morpholino-1-propanol (PPMP) to inhibit $Gb_3$ expression. When present, PPMP is introduced into pre-cultures for at least 6 days prior to cytotoxicity assays and is present for up to drug wash.

Cytotoxicity assays are performed in parallel using HeLa cells subcultured with or without PPMP. Briefly, cells are seeded at a density of 800 cells (25 cm² flasks) and incubated 4 hours prior to treatment to permit adhesion and spreading. Care is taken to avoid contamination of seed cell suspensions by clusters, as their presence introduces major errors in the measurement of clonogenicity.

For determination of the cytotoxicity of holo-NCS or holo-NCS/STxB, sterile aliquots of drug are thawed immediately prior to use, adjusted to the suitable concentration in pH 6.0 PBS and immediately introduced into culture flasks. All experiments are carried out in dim light to prevent photodecomposition of drugs.

The inventors observe that full cytotoxic effect of holo-NCS develops within 6 min incubation only (37° C.), and increasing the length of contact with drug beyond that time does not result in increased cell kill. For this reason the length of exposure to drug was limited to 15-min throughout.

Following treatment, the flasks are washed twice with Hank's balanced salt solution, supplied with fresh medium, and returned to the incubator for 8 days. Colonies are then fixed with methanol, stained and scored.

e) Cytotoxicity Against HeLa Cells

It is first verified that the cytotoxicity of holo-NCS remains unchanged after its coupling to STxB/Cys. Using holo-NCS and holo-NCS/STxB, the concentration of drug that kills 50% of the cell population, is 0.71±0.05 nM. The cytotoxicity of holo-NCS and holo-NCS/STxB is then investigated at 0° C. without and with PPMP, using a lethal concentration of NCS (4 nM). The rationale of this experiment is that holo-NCS is known to be inactive at low temperature (Kappen et al., 1980) while STxB is still able to bind and saturate its receptor under these conditions (Johannes et al., 1997), and is expected to be internalized upon warming up.

Seeded cells in flasks are cooled in ice for 15 min prior to exposure to holo-NCS or holo-NCS/STxB. The drugs (4 nM) are then introduced and incubated for a further 15 min in ice. At that time, the medium is removed by aspiration, and the flasks were carefully rinsed twice with ice-cold Hank's balanced salt solution to remove drugs. The flasks are finally supplied with ice-cold, drug-free medium and allowed to re-equilibrate at room temperature, then incubated at 37° C. for 8 days. Blanks are made to check that no toxicity is introduced by chilling the cells for the duration of the experiment. The results are shown in FIG. 8.

Survival to holo-NCS is in the range 90% or more. Therefore, a low temperature effectively abolishes the cytotoxicity of holo-NCS. In contrast, the holo-NCS/STxB is still active at 0° C., in such a way that cell survival is ca. 30% only. PPMP induced marked resistance to holo-NCS/STxB.

Altogether, the experiment show that STxB is able to carry out drug incorporation into cells under conditions that limit drug uptake by other routes. As the number of receptor sites of STxB at the cell surface is limited, it is suggested that the method will work specifically with drugs acting in the nanomolar range.

In this study we expand the use of STxB as a vector to specifically target tumor cells, and we successfully tested the targeting in mouse models for colorectal cancer. We show that STxB can be orally administered to mice, where it reaches intestinal tumors within 2.5 hours, and shows strong concentration in tumor tissue as compared to control tissue (liver) and normal intestinal tissue. Furthermore, STxB is retained in the tumors even after an incubation period of 24 h. Functionalized STxB is a valuable tool to test novel diagnostic and therapeutic approaches. It is used to study early events in tumor formation in the bowel, which have proven difficult to be visualized with other techniques. RMI studies are undertaken before and after application of a contrast agent bound to STxB in order to better distinguish the tumor from its surrounding tissue. Furthermore, longitudinal studies based on non-invasive imaging techniques are executed with this functionalized agent. Finally, the contrast agents used on human tumors that are grafted orthotopically in the caecum of immunocompromised nude mice.

Furthermore, novel compositions are made using STxB as a carrier that allow for targeting of therapeutic compounds to Gb3 expressing tumors. The effect of these compositions on tumor cells in vitro, on tumors in the described animal models, and on human tumors has been demonstrated.

EXAMPLE 6

Enzyme Delivery for Prodrug Activation

Chemical coupling of β-Glucuronidase to STxB-Cys. 3 mg/ml of purified β-Glucuronidase (β-GUS) in 100 mM HEPES, pH 7.4 is reacted with 90 µM of the heterobifunctional cross linker MBS for 30 min at room temperature. The unreacted MBS is separated from the formed complex β-GUS-MBS by gel filtration through a PBS-EDTA 10 mM equilibrated PD-10 column. The activated β-GUS is then concentrated to 2 mg/ml, mixed with a 35 excess molar of STxB-Cys, and incubated over night at room temperature.

The formed conjugate STxB-Cys-β-GUS is purified by passage on a gel filtration column and an anti-STxB immunoaffinity column. Purified coupling product is highly pure, as tested by Western blotting, and the activity of the enzyme is not altered by the chemical modifications.

Cellular targeting of STxB-Cys coupled β-Glucuronidase. The trafficking proprieties of STxB-Cys-β-GUS are studied in Hela cells, comparatively to β-GUS and STxB-Cys. Hela cells ($0.75 \times 10^5$), grown on glass coverslips, are incubated with 0.5 μM of STxB-Cys, β-GUS or β-GUS-STxB-Cys for 30 min at 4° C. (binding step). The cells are then washed with ice-cold culture medium, shifted to 37° C. for 40 min (internalization step), fixed with 4% PFA for 10 min, permeablized with saponin, stained with the indicated primary and secondary antibodies and analyzed by confocal microscopy. The obtained results are illustrated in FIG. 13.

Figure 13:
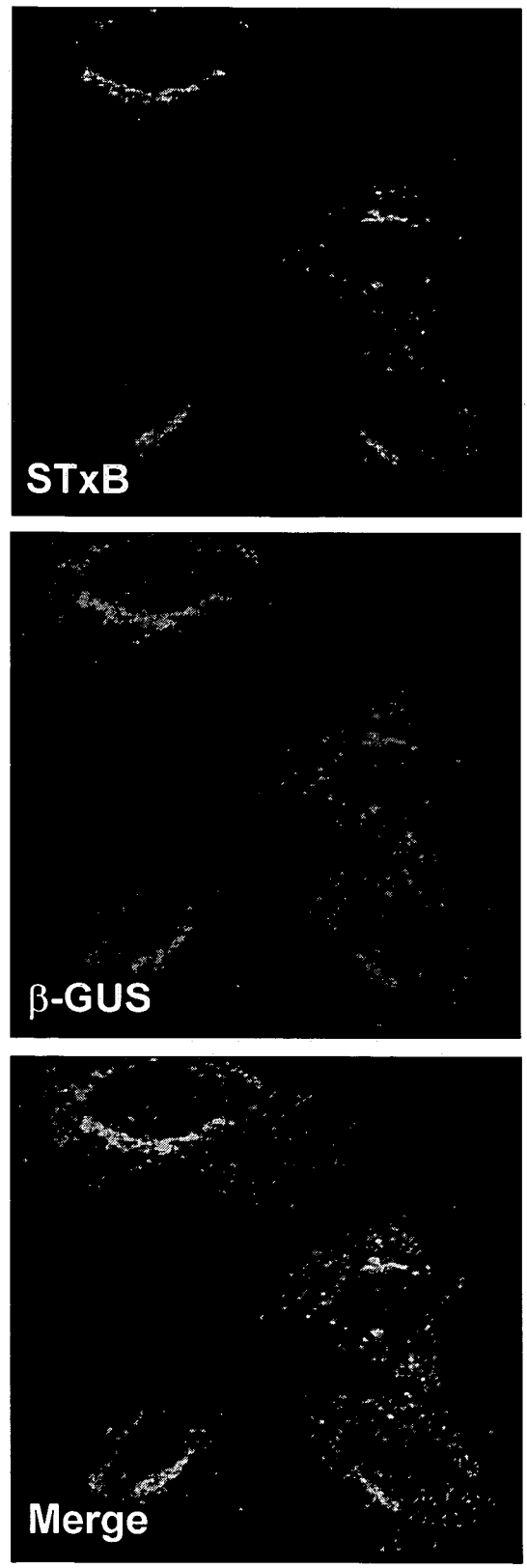

The confocal microscopy experiments show a perfect overlay of the labelling obtained with the antibodies directed against STxB and β-GUS (FIG. 13). No cellular staining is observed in the case of non-vectorized β-GUS (data not shown). These results demonstrate clearly the targeting of β-Glucuronidase into the retrograde transport pathway, using STxB for vectorization.

The results are illustrated on FIG. 13.

Cell associated, vectorized β-Glucuronidase activity. We tested whether vectorization of β-GUS by STxB-Cys results in an increase in cellular enzyme activity in Hela cells expressing or not the Shiga toxin receptor Gb3. The β-GUS enzyme assay is performed in presence of 4-methylumbelliferyl glucuronide, which upon hydrolysis by β-GUS produces fluorescent 4-methylumbelliferone (4-MU), whose fluorescent activity is measured by fluorimetry.

Hela cells ($10^6$) are incubated for 30 min at 4° C. in presence or absence of 0.5 μM STxB-Cys-β-GUS (binding step). After washing with culture medium, cells are shifted to 37° C. for 60 min (internalization step). Cell lysates are prepared in RIPA buffer (PBS 1x, NP40 1%, Doc 0.5%, SDS 0.5%). The basal cellular β-GUS activity and β-GUS activity associated with β-GUS-STxB treated, Gb3 expressing and non-expressing Hela cells are summarized in FIG. 14. Gb3 expressing HeLa cells show a significant increase of β-GUS activity comparatively to non-expressing cells. These latters possess the same level of β-Glucuronidase activity as control cells (basal activity), indicating that cellular targeting of β-GUS activity is dependent on STxB/Gb3 system.

Taken together, our data demonstrate that our approach, based on chemical coupling of β-GUS to STxB-Cys, doesn't alter the enzyme activity of β-GUS and is appropriate to target active enzyme for pro-drug strategies.

Figure 14:
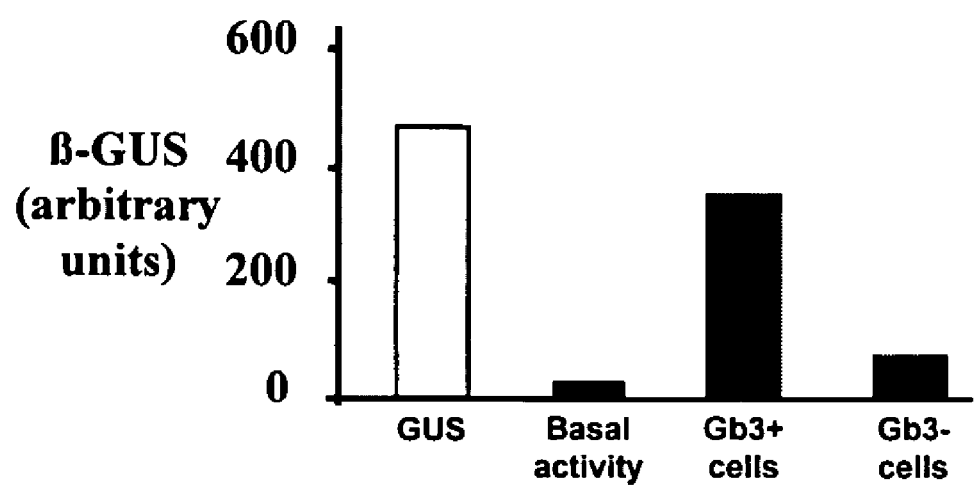

The results are illustrated on FIG. 14.

EXAMPLE 7

Alternative Coupling Methods

Alternatives to coupling via the sulfhydryl groups (—SH) are coupling via amino groups (—NH2), carbohydrates, carboxyls (—COOH), or hydroxyls (—OH). Examples of reactive groups on to-be-vectorized compounds are imidoesters (react on primary amines), N-hydroxysuccinimide esters (react on primary amines), maleimides (react on sulfhydryls), haloacetyls (react on sulfhydryls), hydrazines (react on oxidized carbohydrates), carbodiimides (react on carboxyls).

Wild type STxB is not glycosylated. Glycosylated STxB for chemical coupling can be obtained by expressing a glycosylation site-carrying variant of STxB in glycosylation competent cells, such as the yeast Pichia pastoris. Amino groups, carboxylates, and hydroxyls are present in wild-type STxB, and chemical coupling results in heterogenous mixtures containing inactivated protein. To obtain some degree of site-directed coupling, amino acids with appropriate side chains are fused to the carboxyl terminus of STxB. In one example, the amino acid sequence EDEKKK (Glu-Asp-Glu-Lys-Lys-Lys) (SEQ ID NO: 2) is fused to the carboxyl terminus of wild-type STxB. Reaction with N-hydroxysuccinimide ester-activated biotin allows to introduce biotin onto STxB-EDEKKK (EDEKKK is SEQ ID NO: 2) without inactivating the protein, as exemplified in FIG. 16 in which STxB-vectorized biotin can be detected in the. Golgi apparatus of HeLa cells.

Figure 16:
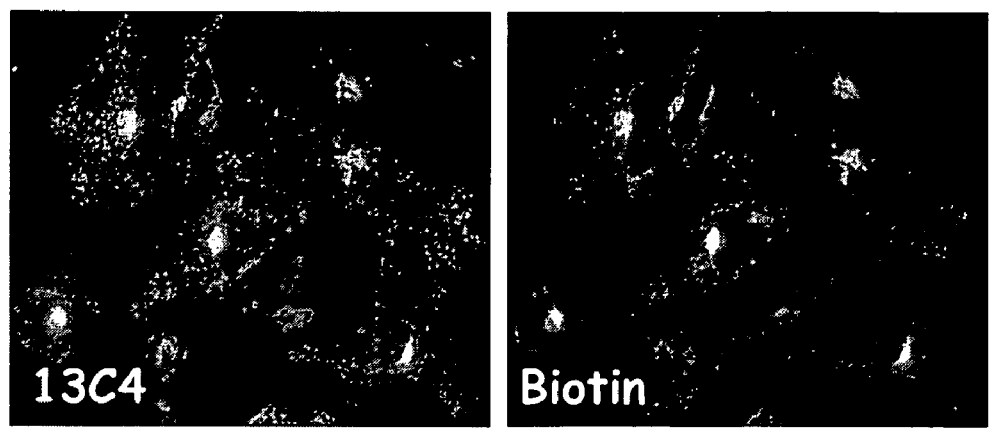

The results are illustrated on FIG. 16.

BIBLIOGRAPHY

Arab, S., E. Russel, W. B. Chapman, B. Rosen, and C. A. Lingwood. 1997. Expression of the verotoxin receptor glycolipid, globotriaosylceramide, in ovarian hyperplasias. *Oncol. Res.* 9:553-563.

Arab, S., J. Rutka, and C. Lingwood. 1999. Verotoxin induces apoptosis and the complete, rapid, long-term elimination of human astrocytoma xenografts in nude mice. *Oncol. Res.* 11:33-39.

Babilon, R. W., K. J. Soprano, and E. E. Henderson. 1985. Hypersensitivity and reduced inhibition of DNA synthesis in ataxia telangiectasia lymphoblasts treated with low levels of neocarzinostatin. *Mutat. Res.* 146:79-87.

Bakina, E., and D. Farquhar. 1999. Intensely cytotoxic anthracycline prodrugs: galactosides. *Anticancer Drug Des.* 14:507-515.

Bligh, E. G., and W. J. Dyer. 1959. A rapid method of total lipid extraction and purification. *Can. J. Biochem. Biophys.* 37:911-917.

Carlsson, J., H. Drevin, and R. Axen. 1978. Protein thiolation and reversible protein-protein conjugation. N-Succinimidyl 3-(2-pyridyidithio) propionate, a new heterobifunctional reagent. *Biochem. J.* 173:723-737.

Clement B et al. 1997, Lomb R, and Möller W (1997) J. Biol. Chem. 272,19615-19620.

Dudouet, B., S. Robine, C. Huet, C. Sahuquillo-Merino, L. Blair, E. Coudrier, and D. Louvard. 1987. Changes in villin synthesis and subcellular distribution during intestinal differentiation of HT29-18 clones. *J. Cell Biol.* 105:359-369.

Falguières, T., F. Mallard, C. Baron, D. Hanau, C. Lingwood, B. Goud, J. Salamero, and L. Johannes. 2001. Targeting of Shiga toxin B-subunit to retrograde transport route in association with detergent resistant membranes. *Mol. Biol. Cell.* 12: 2453-2468.

Favaudon, V. 1982. On the mechanism of reductive activation in the mode of action of some anticancer drugs. *Biochimie.* 64:457475.

Favaudon, V. 1983. Gamma-radiolysis study of the reductive activation of neocarzinostatin by the carboxyl radical. *Biochimie.* 65:593-607.

Fodde, R., W. Edelmann, K. Yang, C. van Leeuwen, C. Carlson, B. Renault, C. Breukel, E. Alt, M. Lipkin, P. M. Khan, and et al. 1994. A targeted chain-termination mutation in the mouse Apc gene results in multiple intestinal tumors. *Proc. Natl. Acad. Sci. USA.* 91:8969-8973.

Gordon, J., H. Mellstedt, P. Aman, P. Biberfeld, M. Bjorkholm, and G. Klein. 1983. Phenotypes in chronic B-lymphocytic leukemia probed by monoclonal antibodies and immunoglobulin secretion studies: identification of stages of maturation arrest and the relation to clinical findings. *Blood.* 62:910-917.

Halazy, S., V. Berges, A. Ehrhard, and C. Danzin. 1990. *Biorg. Chem.* 18:330.

Hamilton, S. R., and L. A. Aaltonen. 2000. WHO classification of tumors: Pathology and genetics of tumors of the digestive system. *Lyon: IARC Press.*

Helbig, R., M. Z. Zdzienicka, and G. Speit. 1995. The effect of defective DNA double-strand break repair on mutations and chromosome aberrations in the Chinese hamster cell mutant XR-V15B. *Radiat Res.* 143:151-157.

Janssen, K. P., F. El Marjou, D. Pinto, X. Sastre, D. Rouillard, C. Fouquet, T. Soussi, D. Louvard, and S. Robine. 2002. Targeted expression of oncogenic K-ras in intestinal epithelium causes spontaneous tumorigenesis in mice. *Gastroenterology,* 123:492-504.

Johannes, L. 2002. The Shiga toxin B-subunit system: Retrograde transport, intracellular vectorization, and more . . . *Am. J. Physiol. Gastrointest Liver Physiol.* 283:G1-G7.

Johannes, L., D. Tenza, C. Antony, and B. Goud. 1997. Retrograde transport of KDEL-bearing B-fragment of Shiga toxin. *J. Biol. Chem.* 272:19554-19561.

Jones, N. L., A. Islur, R. Haq, M. Mascarenhas, M. A. Karmali, M. H. Perdue, B. W. Zanke, and P. M. Sherman. 2000. *Escherichia coli* Shiga toxins induce apoptosis in epithelial cells that is regulated by the Bcl-2 family. *Am. J. Physiol. Gastrointest. Liver Physiol.* 278:G811 -G819.

Kalisiak, A., J. G. Minniti, E. Oosterwijk, L. J. Old, and D. A. Scheinberg. 1991. Neutral glycosphingolipid expression in B-cell neoplasms. *Int. J. Cancer.* 49:837-845.

LaCasse, E. C., M. R. Bray, B. Patterson, W. M. Lim, S. Perampalam, L. G. Radvanyi, A. Keating, A. K. Stewart, R. Buckstein, J. S. Sandhu, N. Miller, D. Banerjee, D. Singh, A. R. Belch, L. M. Pilarski, and J. Gariepy. 1999. Shiga-like toxin-1 receptor on human breast cancer, lymphoma, and myeloma and absence from CD34(+) hematopoietic stem cells: implications for ex vivo tumor purging and autologous stem cell transplantation. *Blood.* 94:2901-2910.

LaCasse, E. C., M. T. Saleh, B. Patterson, M. D. Minden, and J. Gariepy. 1996. Shiga-like toxin purges human lymphoma from bone marrow of severe combined immunodeficient mice. *Blood.* 88:1561-1567.

Lindsey, J. S., I. C. Schreiman, H. C. Hsu, P. C. Kearney, and A. M. Marguerettaz. 1987. Rothemund and Adler-Longo reactions revisited: Synthesis of tetraphenylporphyrins under equilibrium conditions. *J. Org. Chem.* 52:827-836.

Lingwood, C. A. 1996. Role of verotoxin receptors in pathogenesis. *Trends Microbiol.* 4:147-153.

Mallard, F., and L. Johannes. 2002. Shiga toxin B-subunit as a tool to study retrograde transport in: *Methods Mol. Med.* Shiga Toxin Methods and Protocols (Edited by: D Philpott and F Ebel), Vol. 73, Chapter 17:209-220.

Mallard, F., D. Tenza, C. Antony, J. Salamero, B. Goud, and L. Johannes. 1998. Direct pathway from early/recycling endosomes to the Golgi apparatus revealed through the study of Shiga toxin B-fragment transport. *J. Cell Biol.* 143:973-990.

Mangeney, M., Y. Richard, D. Coulaud, T. Tursz, and J. Wiels. 1991. CD77: an antigen of germinal center B cells entering apoptosis. *Eur. J. Immunol.* 21:1131-1140.

Momenteau, M., P. Maillard, M.-A. de Bélinay, D. Carrez, and A. Croisy. 1999. Tetrapyrrolic glycosylated macrocycles for an application in PDT. *J. Biomed. Optics.* 4:1-20.

Mosmann, T. 1983. Rapid colorimetric assay for cellular growth and survival: application to proliferation and cytotoxicity assays. *J. Immunol. Methods.* 65:55-63.

Muller, C., and B. Salles. 1997. Regulation of DNA-dependent protein kinase activity in leukemic cells. *Oncogene.* 15:2343-2348.

Murray, L. J., J. A. Habeshaw, J. Wiels, and M. F. Greaves. 1985. Expression of Burkitt lymphoma-associated antigen (defined by the monoclonal antibody 38.13) on both normal and malignant germinal-center B cells. *Int. J. Cancer.* 36:561-565.

Napier, M. A., B. Holmquist, D. J. Strydom, and I. H. Goldberg. 1981. Neocarzinostatin chromophore: purification of the major active form and characterization of its spectral and biological properties. *Biochemistry.* 20:5602-5608.

Ohtsuki, K., and N. Ishida. 1975. Neocarzinostatin-induced breakdown of deoxyribonucleic acid in HeLa-S3 cells. *J. Antibiot.* (Tokyo). 28:143-148.

Oosterwijk, E., A. Kalisiak, J. C. Wakka, D. A. Scheinberg, and L. J. Old. 1991. Monoclonal antibodies against Gal alpha 1-4 Gal beta 1-4 Glc (Pk, CD77) produced with a synthetic glycoconjugate as immunogen: reactivity with carbohydrates, with fresh frozen human tissues and hematopoietic tumors. *Int. J. Cancer.* 48:848-854.

Povirk, L. F. 1996. DNA damage and mutagenesis by radiomimetic DNA-cleaving agents: bleomycin, neocarzinostatin and other enediynes. *Mutat. Res.* 355:71-89.

Ramegowda, B., and V. L. Tesh. 1996. Differentiation-associated toxin receptor modulation, cytokine production, and sensitivity to Shiga-like toxins in human monocytes and monocytic cell lines. *Infect. Immun.* 64:1173-1180.

Sandvig, K., O. Garred, K. Prydz, J. V. Kozlov, S. H. Hansen, and B. van Deurs. 1992. Retrograde transport of endocytosed Shiga toxin to the endoplasmic reticulum. *Nature.* 358:510-512.

Sandvig, K., and B. van Deurs. 1996. Endocytosis, intracellular transport, and cytotoxic action of Shiga toxin and ricin. *Physiol. Rev.* 76:949-966.

Saxon, E., and C. R. Bertozzi. 2000. Cell surface engineering by a modified Staudinger reaction. *Science.* 287:2007-2010.

Schelté P. et al. "Differential Reactivity of Maleimide and Bromoacetyl functions with Thiols: Application to the Preparation of Liposomal Diepitope Constructs". *Eur. J. Immunol.* (1999) 29: 2297-2308.

Shiloh, Y., E. Tabor, and Y. Becker. 1982. Cellular hypersensitivity to neocarzinostatin in ataxia-telangiectasia skin fibroblasts. *Cancer Res.* 42:2247-2249.

Singhal S. and Kaiser L.R. (1998) Cancer chemotherapy using suicide genes. *Surg. Oncol. Clin. N. Am.* 7: 505-536.

Tatsumi, K., and H. Nishioka. 1977. Effect of DNA Repair systems on antibacterial and mutagenic activity of an antitumor protein, neocarzinostatin. *Mutat. Res.* 48:195-203.

Wen, L., M. Li, and J. B. Schlenoff. 1997. Polyporphyrin thin films from interfacial polymerization of mercaptoporphyrins. *J. Amer. Chem. Soc.* 119:7726-7733.

Wilhelm, C., F. Gazeau, J. Roger, J. N. Pons, M. F. Salis, R. Perzynski, and J. C. Bacri. 2002. Binding of biological effectors on magnetic nanoparticles measured by a magnetically induced transient birefringence experiment. *Phys. Rev. E. Stat. Nonlin. Soft Matter Phys.* 65:031404.

Zemplén, G. 1927. Abbau der reduzierenden biosen. *Ber. Dtsch. Chem. Ges.*: 1555-1564.

The invention claimed is:

1. A hybrid compound for the diagnosis or therapy of cells over-expressing the receptor Gb3 having the following formula STxB-Z(n)-Cys-Y-T wherein
  -STxB is the Shiga Toxin B subunit,
  -Z(n) wherein n is 0 or 1 and when n is 1, Z is an amino acid residue devoid of a sulfhydryl group, or is a polypeptide,
  -Cys is the amino acid residue for Cysteine
    -T is a molecule selected from the group consisting of:
      i) agents for in vivo diagnosis,
      ii) cytotoxic agents,
      ii) prodrugs and
      iv) enzymes for the conversion of a prodrug to a drug,
    -Y is an enzyme cleavable linker between T and Cys, said linker being cleavable for the release of T after the internalization of the hybrid compound into said cells.

2. The hybrid compound according to claim 1 wherein n=0.

3. The hybrid compound according to claim 1, wherein T is a contrast agent for MRI, said contrast agent is a paramagnetic compound.

4. The hybrid compound according to claim 1 wherein T is selected from the group consisting of cytotoxic drugs conjugated with an enzyme-sensitive linker, nucleotide analogs which can stop DNA replication, and amidoximes.

5. The hybrid compound according to claim 1, wherein said enzyme cleavable linker Y is selected from the group consisting of reduced and non-reduced folates cleavable by carboxypeptidase G, phosphate groups from phosphorylated prodrugs cleavable by alkaline phosphatase, hydrolytic cleavable compounds by carboxypeptidase A, nitroreductase for prodrug activation, hydrolysis of lactam ring cleavable by beta-lactamase, amide cleavable by penicillin amidase, cytosine deamidase for prodrug activation, glucuronic acid cleavable by beta-glucoronidase, galactose cleavable by galactosidase and mannose cleavable by mannosidase.

6. The hybrid compound according to claim 4, wherein the enzyme cleavable linker is sensitive to an enzyme, which is endogenous in the over-expressing Gb3 cell or is internalized with a second hybrid compound wherein T is said enzyme.

7. The hybrid compound according to claim 1, wherein T is an enzyme selected from the group consisting of peptidases, thymidine kinase from HSV1, lipases and glyosidases.

8. The hybrid compound according to claim 1, wherein T is a photosensitizing drug for dynamic phototherapies.

9. The hybrid compound according to claim 8, wherein the drug is selected from the group consisting of a dihematoporphyrin ether, a 5-10-15-20-tetra(m-hydroxyphenyl) chlorine, and a glycoconjugated tetrapyrrolic macrocycle.

10. The hybrid compound according to claim 1, wherein T is a holo-Neocarzinostatin.

11. The hybrid compound according claim 9, wherein said glycoconjugated tetrapyrrolic macrocycle is a porphyrin.

12. The hybrid compound according to claim 1, wherein T are prodrugs.

13. The hybrid compound according to claim 1, wherein T are agents for in vivo diagnosis.

14. The hybrid compound according to claim 1, wherein T are cytotoxic agents.

15. A pharmaceutical composition comprising at least one hybrid compound according to claim 1 in combination with a pharmaceutically acceptable carrier.

16. The pharmaceutical composition according to claim 15, containing a first hybrid compound wherein T is a prodrug and a second component for transforming the prodrug into a toxic drug.

17. The pharmaceutical composition according to claim 16, wherein the second component is T, which is an enzyme for transforming said prodrug into a toxic drug.

18. A pharmaceutical composition wherein said first hybrid compound is the hybrid compound according to claim 1 and said second component is a mannosidase.

19. The hybrid compounds according to claim 3, wherein said paramagnetic compound is selected from the group consisting of porphyrin-gadolinium, porphyrin-manganese, synthetic polymer gadolinium, gadolinium-ethoxybenzyl-diethylenetriaminepentaacetic acid, DOPTA-gadolinium, and ferrofluid.

20. The hybrid compounds according to claim 4, wherein the cytotoxic drugs are anthracyclins idarubicin, cisplatinum, mitomycin C, desacetylvinblastine, methotrexate, N-acetylmelphan, 5-fluorouracil, nitrogen mustards, calicheamicin or maytansinoids.

21. The hybrid compounds according to claim 20, wherein the anthracyclins are daunomycin, doxorubicin or daunorubicin.

22. The hybrid compounds according to claim 4, wherein the nucleotide analogs which can stop DNA replication are gangciclovir or acyclovir.

23. A hybrid compound for the diagnosis or therapy of cells over-expressing the receptor Gb3 having the following formula STxB-Z(n)-Cys-Y-T wherein
-STxB is the Shiga Toxin B subunit,
-Z(n) wherein n is 0 or 1 and when n is 1, Z is an amino acid residue devoid of a sulfhydryl group, or is a polypeptide,
-Cys is the amino acid residue for Cysteine
-T is a molecule selected from the group consisting of:
  i) agents for in vivo diagnosis,
  ii) cytotoxic agents,
  iii) prodrugs and
  iv) enzymes for the conversion of a prodrug to a drug,
-Y is an enzyme cleavable linker between T and Cys, said linker being cleavable for the release of T after the interualization of the hybrid compound into said cells wherein said enzyme cleavable linker Y is selected from the group consisting of reduced and non-reduced folates cleavable by carboxypeptidase G, phosphate groups from phosphorylated prodrugs cleavable by alkaline phosphatase, hydrolytic cleavable compounds by carboxypeptidase A, nitroreductase for prodrug activation, hydrolysis of lactam ring cleavable by beta-lactamase, amide cleavable by penicillin amidase, cytosine deamidase for prodrug activation, glucuronic acid cleavable by beta-glucoranidase, galactose cleavable by galactosidase; and mannose cleavable by mannosidase.

* * * * *

SEQUENCE LISTING

<160> NUMBER OF SEQ ID NOS: 2

<210> SEQ ID NO 1
<211> LENGTH: 91
<212> TYPE: PRT
<213> ORGANISM: Artificial Sequence
<220> FEATURE:
<223> OTHER INFORMATION: Description of Artificial Sequence: synthetic peptide

<400> SEQUENCE: 1

His Met Lys Lys Thr Leu Leu Ile Ala Ala Ser Leu Ser Phe Phe Ser
1               5                   10                  15

Ala Ser Ala Leu Ala Thr Pro Asp Cys Val Thr Gly Lys Val Glu Tyr
            20                  25                  30

Thr Lys Tyr Asn Asp Asp Asp Thr Phe Thr Val Lys Val Gly Asp Lys
        35                  40                  45

Glu Leu Phe Thr Asn Arg Trp Asn Leu Gln Ser Leu Leu Leu Ser Ala
    50                  55                  60

Gln Ile Thr Gly Met Thr Val Thr Ile Lys Thr Asn Ala Cys His Asn
65                  70                  75                  80

Gly Gly Gly Phe Ser Glu Val Ile Phe Arg Cys
                85                  90

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: synthetic peptide

<400> SEQUENCE: 2

Glu Asp Glu Lys Lys Lys
1               5